US008859252B1

(12) United States Patent
Mitschelen et al.

(10) Patent No.: US 8,859,252 B1
(45) Date of Patent: Oct. 14, 2014

(54) PROSTATIC ACID PHOSPHATASE, COMPOSITIONS COMPRISING THE SAME, AND METHODS FOR PRODUCING AND/OR PURIFYING THE SAME

(71) Applicant: Aerial BioPharma LLC, Morrisville, NC (US)

(72) Inventors: Jonathan Mitschelen, Oklahoma City, OK (US); John Lightholder, Oklahoma City, OK (US); Gary Bream, Cary, NC (US); Kenneth Freeman, Holly Springs, NC (US)

(73) Assignee: Aerial BioPharma, LLC, Morrisville, NC (US)

( * ) Notice: Subject to any disclaimer, the term of this patent is extended or adjusted under 35 U.S.C. 154(b) by 0 days.

(21) Appl. No.: 14/146,165

(22) Filed: Jan. 2, 2014

(51) Int. Cl.
 C12N 9/16 (2006.01)
 A61K 38/00 (2006.01)
 C07K 14/47 (2006.01)

(52) U.S. Cl.
 CPC .................................... *C12N 9/16* (2013.01)
 USPC ........................................ 435/196; 435/69.1

(58) Field of Classification Search
 None
 See application file for complete search history.

(56) References Cited

U.S. PATENT DOCUMENTS

| 4,205,130 | A | 5/1980 | Vihko |
| 7,091,004 | B1 | 8/2006 | Morris et al. |
| 7,094,533 | B1 | 8/2006 | Lin |
| 8,512,983 | B2 | 8/2013 | Gawlitzek et al. |
| 2010/0266569 | A1 | 10/2010 | Zylka et al. |
| 2011/0081700 | A1 | 4/2011 | Hasslacher et al. |
| 2013/0209438 | A1 | 8/2013 | Zylka et al. |
| 2013/0317197 | A1 | 11/2013 | Lihme et al. |

FOREIGN PATENT DOCUMENTS

| WO | WO 2005/014849 | 2/2005 |
| WO | WO 2006/051172 | 5/2006 |
| WO | WO 2008/039021 | 4/2008 |
| WO | WO 2008/098979 | 8/2008 |
| WO | WO 2009/064497 | 5/2009 |
| WO | WO 2011/150110 | 12/2011 |

OTHER PUBLICATIONS

Vihko et al. "Rat acid phosphatase: Overexpression of active, secreted enzyme by recombinant baculovirus-infected insect cells, molecular properties and crystallization" 1993 Proc Natl Acad Sci 90 799-803.*
Al-Samarrai et al., Isolation and Purification of Acid Phosphatase from Human Seminal Fluid, Mar. 2007, 3(5): 23-34.
Chen et al., Antinociceptive Effect of Prostatic Acid Phosphatase in a Rat Model of Cancer-induced Bone Pain, *Pain Physician* Nov./Dec. 2013, 16: 533-546.
GenBank® Accession Nos. NM_019807. Sowa et al., Recombinant mouse PAP has pH-dependent ectnonueclotidase activity and acts through A(1)-adenosine receptors to mediate antinociceptions, *PLoS ONE* 2009, 4(1): E4248.
GenBank® Accession Nos. NM_207668. Sowa et al., Recombinant mouse PAP has pH-dependent ectnonueclotidase activity and acts through A(1)-adenosine receptors to mediate antinociceptions, *PLoS ONE* 2009, 4(1): E4248.
GenBank® Accession Nos. NP_062781. Sowa et al., Recombinant mouse PAP has pH-dependent ectnonueclotidase activity and acts through A(1)-adenosine receptors to mediate antinociceptions, *PLoS ONE* 2009, 4(1): E4248.
GenBank® Accession Nos. NP_997551. Sowa et al., Recombinant mouse PAP has pH-dependent ectnonueclotidase activity and acts through A(1)-adenosine receptors to mediate antinociceptions, *PLoS ONE* 2009, 4(1): E4248.
Gonda, I., Aerosols for Delivery of Therapeutic and Diagnostic Agents to the Respiratory Tract, *Critical Reviews in Therapeutic Drug Carrier Systems* 1990, 6:273-313 (Abstract Only).
Herrala et al., Purification of Prostatic Acid Phosphatase (PAP) for Structural and Functional Studies, *Methods in Molecular Biology* 2013, 1053: 167-178.
Novoprotein, Recombinant Human ACPP: Catalog #C420 Dervied From Human Cells, www.novoprotein.com, Jan. 2014.
Ostanin et al., Heterologous expression of human prostatic acid phosphatase and site-directed mutagenesis of the enzyme active site, *The Journal of Biological Chemistry* 1994, 269(12): 8971-8978.
Paoli et al., Purification of human prostatic acid phosphatase and preparation of a specific antiserum in the rabbit, *Italian Journal of Biochemistry* May-Jun. 1981, 30(3): 242-250.
Porvari et al., Site-directed Mutagenesis of Prostatic Acid Phosphatase, *The Journal of Biological Chemistry* Sep. 9, 1994, 269(36): 22642-22646.
Porvari et al., Differential androgen regulation of rat prostatic acid phosphatase transcripts, Biochemical and Biophysical Research Communications 1995, 213(3): 861-868.
Raeburn et al., Techniques for drug delivery to the airways, and the assessment of lung function in animal models, *Journal of Pharmacological and Toxicological Methods* 1992, 27: 143-159 (Abstract Only).
Roiko et al., Primary structure of rat secretory acid phosphatase and comparison to other acid phosphatases, *Gene* 1990, 89: 223-229.
Rusciano et al., One-Step, High-Yield Purification of Human Prostatic Acid Phosphatase from Seminal Fluid by Gel-Filtration HPLC under Nondenaturing Conditions, *Clinical Chemistry* 1988, 34(5): 984-986.
Schneider et al., Three-dimensional structure of rat acid phophatase, *The EMBO Journal* 1993, 12(7): 2609-2615.
Sino Biological Inc., Recombinant Human ACPP/PSAP: Catalog No. 10959-H08H, www.sinobiological.com, Dec. 2013.
Sowa et al., Recombinant Mouse PAP has pH-Dependent Ectonucleotidase Activity and Acts through A1-Adenosine Receptors to Mediate Antinociception, *PLoS ONE* 2009, 4(1): 1-7.

(Continued)

*Primary Examiner* — Suzanne M Noakes
*Assistant Examiner* — Gerard Lacourciere
(74) *Attorney, Agent, or Firm* — Myers Bigel Sibley & Sajovec, P.A.

(57) ABSTRACT

The present invention relates generally to prostatic acid phosphatase (PAP), compositions comprising the same, and methods for producing and/or purifying the same.

30 Claims, 1 Drawing Sheet

(56) References Cited

OTHER PUBLICATIONS

Vihko et al., Purification of Human Prostatic Acid Phosphatase by Affinity Chromatography and Isoelectric Focusing. Part I., *Clinical Chemistry* 1978, 24(3): 466-470.

Vihko et al., Characterization of the Principle Human Prostatic Acid Phosphatase Isoenzyme, Purified by Affinity Chromatography and Isoelectric Focusing. Part II, *Clinical Chemistry* 1978, 24(3): 1783-1787.

Vihko et al., Serum Prostate-Specific Acid Phosphatase: Development and Validation of a Specific Radioimmunoassay, *Clinical Chemistry* 1978, 24(11): 1915-1919.

Vihko et al., Molecular cloning and sequence analysis of cDNA encoding human prostatic acid phosphatase, *FEBS Letters* 1988, 236(2): 275-281.

Vihko et al., Rat acid phosphatase: Overexpression of active, secreted enzyme of recombinant baculovirus-infected insect cells, molecular properties, and crystallization, *Proceedings of The National Academy of Sciences* Feb. 1993, 90: 799-803.

Yoshiki et al., Single-step purification of prostatic acid phosphatase: immunoaffinity chromatography with a monoclonal antibody, *International Journal of Urology* Sep. 1995, 2(4): 261-266.

\* cited by examiner

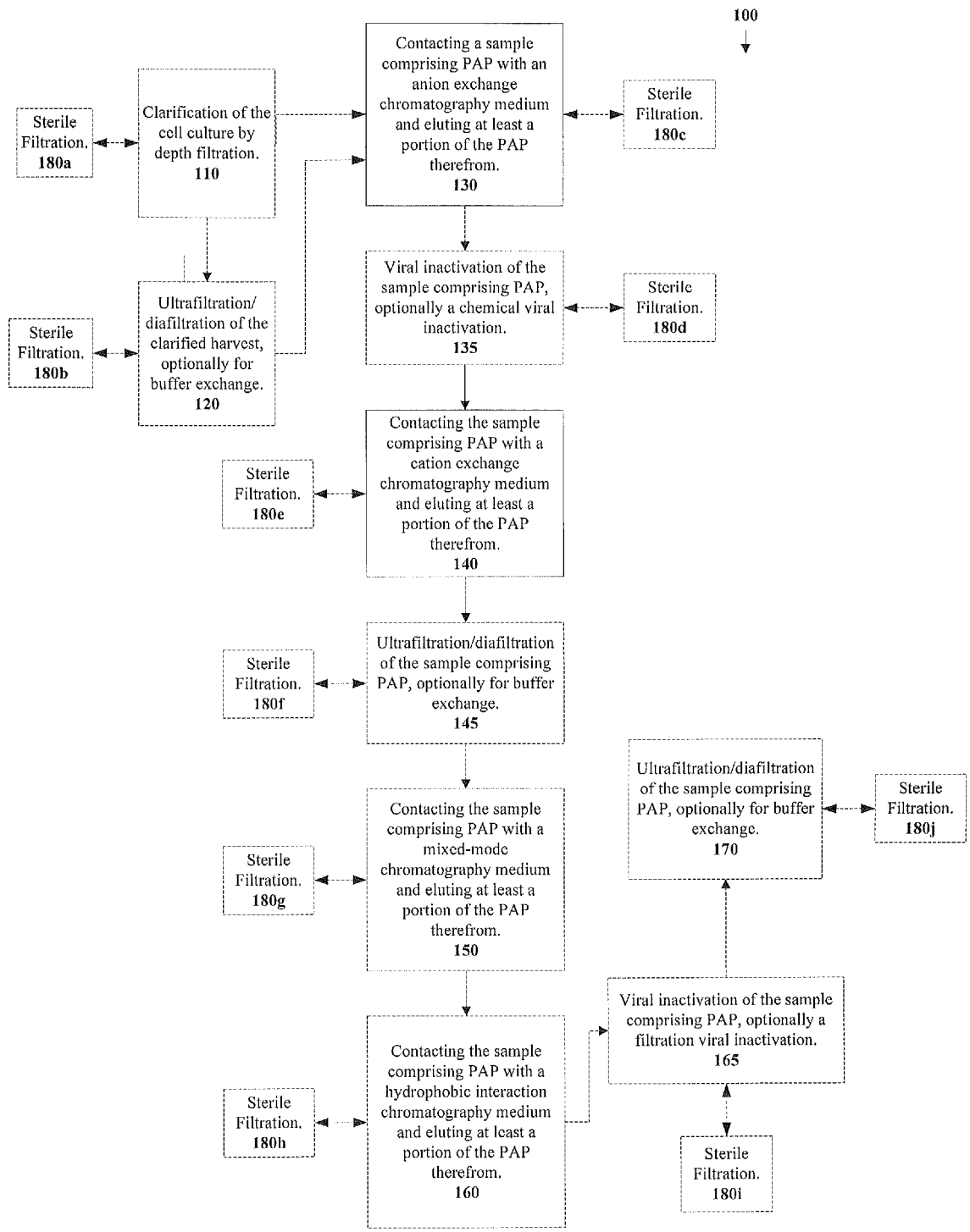

PROSTATIC ACID PHOSPHATASE, COMPOSITIONS COMPRISING THE SAME, AND METHODS FOR PRODUCING AND/OR PURIFYING THE SAME

STATEMENT REGARDING ELECTRONIC FILING OF A SEQUENCE LISTING

A Sequence Listing in ASCII text format, submitted under 37 C.F.R. §1.821, entitled 9798-15_ST25.txt, 5,334 bytes in size, generated on Dec. 23, 2013 and filed via EFS-Web, is provided in lieu of a paper copy. This Sequence Listing is hereby incorporated by reference into the specification for its disclosures.

BACKGROUND

Prostatic acid phosphatase (PAP) is an enzyme in the histidine acid phosphatase family that can hydrolyze phosphomonoesters, such as 5'-nucleoside monophosphates. There are both secretory and transmembrane forms of PAP, which can be produced by the prostate. Human PAP is a homodimer with a molecular weight of about 100 kDa. Research has demonstrated that PAP can serve as a marker for prostate cancer and can be used to treat pain, such as chronic pain.

The present invention addresses previous shortcomings in the art by providing PAP, compositions comprising the same, and methods for producing and/or purifying PAP.

SUMMARY OF EMBODIMENTS

A first aspect of the present invention is directed to prostatic acid phosphatase (PAP) having a purity of greater than 60%. In one embodiment, the purity of the PAP provided herein may be greater than 80%, greater than 95%, or even greater than 98%. Purity, in one embodiment, is measured by gel electrophoresis. The PAP may be isolated according to some embodiments of the present invention. In one embodiment, the PAP may be isolated from a host cell. The PAP may have a host cell protein content of less than about 100 ng host cell protein per mg PAP and/or a host cell DNA content of less than about 100 pg host cell DNA per mg PAP. The PAP, in one embodiment, may be recombinant PAP, optionally obtained from a mammalian cell, for example, a human cell. The PAP may be obtained, purified, and/or produced according to a method of the present invention.

A second aspect of the present invention is directed to compositions, pharmaceutical compositions, and medicaments including PAP according to embodiments of the present invention. The PAP may be obtained, purified, and/or produced according to a method of the present invention.

Another aspect of the present invention is directed to a method of treating a subject comprising administering a pharmaceutical composition and/or medicament of the present invention. In one embodiment, a method of treating pain in a subject may be provided by administering a pharmaceutical composition and/or medicament of the present invention.

A further aspect of the present invention is directed to a method for purifying PAP from a mixture. The method may include, in one embodiment, purifying PAP from a mixture by subjecting the mixture to two or more chromatography steps chosen from anion exchange chromatography, cation exchange chromatography, mixed-mode chromatography, and hydrophobic interaction chromatography, thereby providing purified PAP.

Another aspect of the present invention is directed to a method of culturing a mammalian cell expressing a recombinant PAP. The method, in one embodiment, may include culturing the mammalian cell in a defined serum-free base medium during a growth phase and maintaining the mammalian cell in the base medium during a production phase by supplementing the base medium with a defined serum-free feed medium.

The foregoing and other aspects and embodiments of the present invention are described in detail below.

BRIEF DESCRIPTION OF THE DRAWING

FIG. 1 shows a purification method according to embodiments of the present invention.

DETAILED DESCRIPTION

The present invention will now be described more fully hereinafter. This invention may, however, be embodied in different forms and should not be construed as limited to the embodiments set forth herein. Rather, these embodiments are provided to fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention.

All publications, patent applications, patents and other references cited herein are incorporated by reference in their entirety for all purposes relevant to the sentence and/or paragraph in which the reference is presented. In case of a conflict in terminology, the present specification is controlling.

As used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination.

Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz*, 537F.2d 549, 551-52, 190 U.S.P.Q. 461, 463 (CCPA 1976) (emphasis in the original); see also MPEP §2111.03. Thus, the term "consisting essentially of" as used herein should not be interpreted as equivalent to "comprising."

The term "about," as used herein when referring to a measurable value, such as an amount or concentration and the like, is meant to refer to variations of up to ±20% of the specified value, such as, but not limited to, ±10%, ±5%, ±1%, ±0.5%, or even ±0.1% of the specified value, as well as the specified value. For example, "about X" where X is the measurable value, can include X as well as a variation of ±20%, ±10%, ±5%, ±1%, ±0.5%, or ±0.1% of X. A range provided herein for a measurable value may include any other range and/or individual value therein.

Provided herein are methods for producing PAP and/or purifying PAP from a sample or mixture. The methods of the present invention may be used for both small and large scale PAP manufacture, production, and/or purification. In some embodiments, the methods described herein provide for a large scale manufacture, production, and/or purification of PAP at the 100 L or more bioreactor scale.

The production and/or purification methods provided herein may be used to produce and/or purify PAP from any organism that expresses PAP. In certain embodiments, PAP may be obtained from a mammal, such as, but not limited to, a human, bovine, rat, and/or mouse. PAP may be a naturally occurring PAP. A "naturally occurring PAP" as used herein refers to a PAP that may be isolated from the organism from which it is derived, such as, but not limited to, a mammal. Alternatively, PAP may be obtained by expressing it in a host cell, such as, but not limited to, a mammalian, yeast, bacteria, or insect host cell, and thus may be a recombinant PAP. Recombinant PAP may be expressed by cells in culture with the culture having PAP titers (i.e., a PAP concentration) of at least about 100 mg/L, 150 mg/L, 200 mg/L, 250 mg/L, 300 mg/L, 350 mg/L, 400 mg/L, 550 mg/L, 500 mg/L, or more. In certain embodiments, recombinant PAP may be expressed in cell culture in a range of about 50 mg/L to about 700 mg/L or about 100 mg/L to about 500 mg/L. The concentration of PAP in a sample or composition may be determined using methods known to those of skill in the art, such as, but not limited to, by using enzyme activity assays. In some embodiments, PAP may be a recombinant, human PAP, optionally obtained from a mammalian cell. Recombinant PAP produced in a host cell may be found as a soluble protein, an insoluble protein, or any combination thereof. Non-limiting examples of human PAP that may be used with the present invention include, but are not limited to, those corresponding to Accession Nos. P15309.3, AAA60021.1, AAB60640.1, AAA69694.1, AAA60022.1,
XP_005247624.1, NM_001099.4, P15309-1, P15309-2, P15309-3, SEQ ID NO:1, and SEQ ID NO:2.

The production and/or purification methods provided herein may be used to produce and/or purify secretory and/or transmembrane PAP that is optionally soluble. "Soluble" as used herein means that at least a portion of the PAP is not present in insoluble protein aggregates. In some embodiments, a soluble PAP may be dissolved in a solution (e.g., cell culture medium, bodily fluid, buffer, etc.) in which it is present to provide a clear to slightly opalescent solution with no visible particulates, as assessed by visual inspection. In some embodiments, PAP may be the secretory form of PAP, optionally soluble. In certain embodiments, PAP may be human, secretory PAP, optionally soluble, and the secretory, optionally soluble, human PAP may be recombinant.

"Purifying" as used herein refers to removing, isolating, separating, and/or the like PAP in a sample or mixture from at least one impurity or contaminant present in the sample or mixture. The terms "sample" and "mixture" are used interchangeably herein and may include a composition comprising PAP. "Impurities" and "contaminants", and their grammatical variants, are used interchangeably herein and include, but are not limited to, cellular components (e.g., host cell components, such as proteins, nucleic acids, and/or lipids), bodily tissues or fluids, and/or culture medium. PAP may have a purity of about 50% or more, such as, but not limited to, about 55%, 60%, 65%, 70%, 75%, 80%, 85%, 90%, 91%, 92%, 93%, 94%, 95%, 96%, 97%, 98%, 99%, or more. In some embodiments, PAP may have a purity of greater than 95%, 98%, 98.5%, 99%, or 99.5%. In certain embodiments, PAP may have a purity of about 60% to about 100%, about 75% to about 100%, about 90% to about 100%, about 95% to about 100%, or about 98% to about 100%. PAP may be purified according to a method of the present invention.

A method of the present invention may provide a substantially purified PAP. "Substantially purified" or "substantially pure", as used herein, refers to a PAP that has a purity of at least 50%. In some embodiments, a substantially purified PAP may have a purity of at least 60%; in certain embodiments, at least 95%; and in yet further embodiments, at least 98%. Thus, substantially pure PAP may be at least 50% free of impurities, such as, but not limited to, host cell proteins.

A method of the present invention may provide a composition comprising PAP that has a host cell protein (HCP) content and/or host cell DNA (HCD) content of less than about 300 ng/mg PAP, such as, but not limited to, less than about 250 ng/mg PAP, 200 ng/mg PAP, 150 ng/mg PAP, 100 ng/mg PAP, 75 ng/mg PAP, 50 ng/mg PAP, 750 pg/mg, 500 pg/mg, 250 pg/mg, 100 pg/mg, 50 pg/mg, or 25 pg/mg. In some embodiments, PAP may have a host cell protein content of less than about 100 ng host cell protein per mg PAP and/or may have a host cell DNA content of less than about 100 pg host cell DNA per mg PAP. In some embodiments, a method of the present invention may provide a composition comprising PAP that has a host cell protein content and/or host cell DNA content of less than about 100 ppm or 100 ng/mg PAP; in certain embodiments, less than about 50 ppm or 50 ng/mg PAP; in further embodiments; less than about 25 ppm or 25 ng/mg PAP; and in yet further embodiments, less than about 10 ppm or 10 ng/mg PAP.

The overall or total recovery (i.e., yield) of PAP after a method of the present invention and/or after one or more step(s) in a method of the present invention may be about 20% or more, such as, but not limited to, about 25%, 30%, 35%, 40%, 45%, 50%, 55%, 60%, 65%, 70%, 75%, 80%, 85%, 90%, 95%, or more. In some embodiments, a method of the present invention may provide an overall recovery of PAP of about 20% to about 95%, about 30% to about 90%, about 35% to about 75%, or about 30% to 50%.

The removal of impurities may result in enrichment of PAP. "Enrichment," "enriching," and grammatical variants thereof as used herein refer to an increase in the percent of PAP in a sample. Accordingly, enrichment of PAP occurs when the percent of PAP is increased in a sample after some manipulation of the sample, such as, for example, subjecting the sample to one or more chromatographic steps. In some embodiments, a sample comprising PAP may be enriched by at least about a 10-fold reduction of impurities, such as, but not limited to, host cell proteins, in the sample. In certain embodiments, a sample comprising PAP may be enriched by at least about a 20-fold, 30-fold, 40-fold, 50-fold, 60-fold, 70-fold, 80-fold, 90-fold, 100-fold, or more reduction of impurities in the sample.

Methods known to those of skill in the art may be used to determine the purity of PAP and/or the fold reduction of impurities in a sample comprising PAP. For example, PAP may be analyzed by gel electrophoresis, such as, but not limited to, SDS-PAGE, to determine the purity of PAP. Assays and methods, such as, but not limited to, those described in U.S. Patent Application Publication No. 2011/0081700, the contents of which are incorporated herein by reference in their entirety, may be used to measure impurities, such as, but not limited to, host cell proteins, in a sample comprising PAP and to calculate the fold reduction of impurities. In certain embodiments, host cell proteins may be detected, for example, by immunochemical methods using polyclonal antisera.

According to some embodiments of the present invention, methods of purifying PAP from a mixture comprising PAP are provided. The mixture may comprise cell culture medium and/or a buffer. A method of the present invention may include one or more purification and/or chromatography steps and/or techniques such as, but not limited to, filtration, centrifugation, precipitation, phase separation, affinity purification, gel filtration, ion exchange chromatography (e.g., anion and/or cation exchange chromatography), hydrophobic interaction chromatography, high performance liquid chromatography (HPLC), mixed-mode chromatography, and any combination thereof. In some embodiments, a method of the present invention does not comprise affinity chromatography, gel filtration chromatography, and/or protein precipitation.

A chromatography step may be carried out by contacting a mixture comprising PAP with a chromatography medium, such as, but not limited to, a chromatography resin, under conditions suitable to allow at least a portion of the PAP to be purified from the mixture. The chromatography medium contacted with the mixture may include, but is not limited to, an anion exchange resin, a cation exchange resin, a mixed-mode resin, and/or a hydrophobic interaction resin. "Contacting" as used herein in regard to a chromatography step includes placing, adding, loading, mixing, washing, chromatographically contacting and the like the mixture with a chromatography resin. "Chromatographically contacting" as used herein refers to contacting a mixture to be separated with a chromatographic medium, such as, but not limited to, a resin, using any mode of chromatography described herein and/or known in the art. Modes include, but are not limited to, batch-mode and column chromatography. Appropriate column dimensions can be determined by those skilled in the art. Chromatographically contacting may be effected by exposing and/or incubating the mixture on, in, and/or within the medium; filtering the mixture through the medium; or by any other means known to those of skill in the art.

A method of the present invention may comprise two or more chromatography steps, such as, but not limited to, two, three, four, five, six, seven, or more chromatography steps. In some embodiments, a method of purifying PAP may comprise providing a mixture comprising PAP; and purifying the mixture by subjecting the mixture to two or more chromatography steps chosen from or selected from the group consisting of anion exchange chromatography, cation exchange chromatography, mixed-mode chromatography, and hydrophobic interaction chromatography to provide a purified PAP. As those skilled in the art will understand, the two or more chromatography steps may be carried out in any order.

In some embodiments, a PAP purification method of the present invention comprises at least four chromatography steps, which may comprise the following chromatography medium: anion exchange chromatography, cation exchange chromatography, mixed-mode chromatography, and hydrophobic interaction chromatography. In certain embodiments, each of the following chromatography media are used in the following order: anion exchange chromatography, cation exchange chromatography, mixed-mode chromatography, and hydrophobic interaction chromatography, but other steps, including other chromatography steps, may be included between one or more of the chromatography steps.

A buffer may be used in a method of the present invention. In some embodiments, PAP may be present in a buffer to provide a sample comprising PAP. Exemplary buffers include, but are not limited to, borate buffers, triethanolamine/iminodiacetic acid buffers, tris(hydroxymethyl)aminomethane (Tris) buffers, acetate buffers, ammonium acetate buffers, tricine buffers, bicine buffers, N-[tris(hydroxymethyl)methyl]-2-aminoethanesulfonic acid (TES) buffers, 4-(2-hydroxyethyl)piperazine-1-ethanesulfonic acid (HEPES) buffers, [(2-Hydroxy-1,1-bis(hydroxymethyl)ethyeamino]-1-propanesulfonic acid (TAPS) buffers, and phosphate buffers. A buffer may have a pH of at least about 4, such as, but not limited to, about 4.5, 5, 5.5, 6, 6.5, 7, 7.5, 8, 8.5, 9, or more. A buffer may have a pH in a range of about 5 to about 9, such as, but not limited to, about 6 to about 8, or about 6.5 to about 7.5.

A purifying step of a method of the present invention may comprise contacting a mixture comprising PAP with a chromatography medium and eluting the PAP from the chromatography medium to obtain an eluate. An eluate may be subjected to one or more steps according to embodiments of the present invention. For example, an eluate may be subjected to steps, such as, but not limited to, buffer exchange, filtration, and/or viral inactivation. Alternatively or in addition, an eluate may be subjected to a chromatography step.

In some embodiments, a method of purifying PAP may comprise contacting a mixture comprising PAP with an anion exchange chromatography medium; eluting PAP from the anion exchange chromatography medium to obtain a first eluate; contacting the first eluate with a cation exchange chromatography medium; eluting PAP from the cation exchange chromatography medium to obtain a second eluate; contacting the second eluate with a mixed-mode chromatography medium; eluting PAP from the mixed-mode chromatography medium to obtain a third eluate; contacting the third eluate with a hydrophobic interaction chromatography medium; and eluting PAP from the hydrophobic interaction chromatography medium to obtain a fourth eluate. In some embodiments, one or more additional step(s) may be included before and/or after one or more of the contacting steps; thus, the first eluate, second eluate, third eluate, and/or fourth eluate may have a different composition when contacted with a chromatography medium compared to after elution from a chromatography medium. The first eluate, second eluate, third eluate, and/or fourth eluate, however, may comprise at least a portion or all of the PAP eluted in their respective chromatography steps. For example, the method may comprise a buffer exchange after the first contacting step; thus, the first eluate may have a different composition (e.g., a different buffer) compared to the composition of the first eluate prior to the buffer exchange but the buffer exchanged first eluate may comprise at least a portion or all of the PAP eluted after the anion exchange chromatography step.

A method of the present invention may comprise contacting a mixture comprising PAP with a first chromatography medium; eluting at least a portion of the PAP from the first chromatography medium to obtain a first PAP sample; contacting at least a portion of the first PAP sample with a second chromatography medium; and eluting at least a portion of the PAP from the second chromatography medium to obtain a second PAP sample. The chromatography steps may be repeated with the same and/or different chromatography media until PAP with a desired purity is obtained.

In some embodiments, a method of the present invention comprises contacting a mixture comprising PAP with an anion exchange chromatography medium; eluting at least a portion of the PAP from the anion exchange chromatography medium to obtain a first PAP sample; contacting at least a portion of the first PAP sample with a cation exchange chromatography medium; eluting at least a portion of the PAP from the cation exchange chromatography medium to obtain a second PAP sample; contacting at least a portion of the second PAP sample with a mixed-mode chromatography medium; eluting at least a portion of the PAP from the mixed-mode chromatography medium to obtain a third PAP sample; contacting at least a portion of the third PAP sample with a hydrophobic interaction chromatography medium; and eluting PAP from the hydrophobic interaction chromatography medium to obtain a fourth PAP sample.

Exemplary materials that may be used in a purification method of the present invention, such as, but not limited to, chromatography medium, are described herein.

Anion exchange chromatography relies on charge-charge interactions between the components in the sample, such as, for example, proteins, and the charges immobilized on the anionic chromatography medium. In anion exchange chromatography, the binding ions of the components are negative and the immobilized functional group of the chromatography medium is positive. Exemplary anionic exchange chromatography medium include, but are not limited to, resins, monoliths, or membranes. In some embodiments, an anionic exchange chromatography medium is in the form of a column comprising anion exchange chromatography resin.

Strong anion exchange media may comprise a quaternary ammonium ion and weak anion exchange media may comprise a tertiary and/or secondary amine functional group, such as a diethylaminoethyl (DEAE) group. Exemplary functional groups anion exchange medium may comprise include, but are not limited to, quaternary ammonium groups such as quaternary alkylamines and quaternary alkylalkanol amines, diethylamine groups, diethylaminopropyl groups, amino groups, trimethylammoniumethyl groups, trimethylbenzyl ammonium groups, dimethylethanolbenzyl ammonium groups, and polyamine groups. Anion-exchange resins may comprise a counter ion, such as, but not limited to, a chloride ion (Cl⁻), which may maintain electroneutrality.

Exemplary anion exchange membranes include, but are not limited to, SARTOBIND® Q from Sartorius, MUSTANG® Q from Pall Technologies and INTERCEPT® Q membrane, from Millipore.

Exemplary anionic exchange resins, include, but are not limited to, those that comprise a quaternary aminoethyl (QAE) moiety such as, for example, TOYOPEARL® QAE (available from Tosoh Bioscience, Germany) and SELECTA-CEL® QAE (a quaternary aminoethyl derivative of cellulose, available from Polysciences Inc., Pennsylvania USA); quaternary ammonium (Q) moiety such as, for example, Q SEPHAROSE®, Q SEPHAROSE® XL, Q SEPHAROSE® FF, Q SEPHAROSE® HP (available from GE Healthcare, Germany), Resource™ Q (available from GE Healthcare, Germany), MACRO-PREP® High Q (Bio-Rad, California, USA), TOYOPEARL® Super Q (available from Tosoh Bioscience, Germany), and UNOsphere™ Q (available from Bio-Rad, California, USA); and a trimethylammoniumethyl (TMAE) group, such as, for example, FRACTOGEL® EMD TMAE (available from Merck, Germany) and ESHMUNO® Q (available from EMD Millipore, Germany). Further exemplary anion exchange chromatography medium include, but are not limited to, those described in U.S. Patent Application No. 2013/0317197, the contents of which are incorporated herein by reference in their entirety.

An anionic exchange chromatography medium according to embodiments of the present invention may comprise a resin having a hydrophilic polymer matrix, such as, but not limited to, a polyvinylether polymer. The resin may comprise a tentacle structure comprising the hydrophilic polymer matrix with anionic exchange functional groups, such as, but not limited to, trimethylammoniumethyl, at the end of the tentacle structure. In some embodiments, an anionic exchange resin in embodiments of the present invention comprises a trimethylammoniumethyl functional group. In some embodiments, an anionic exchange resin of the present invention comprises a quaternary ammonium moiety and/or a quaternary amine moiety. An anionic exchange chromatography medium according to embodiments of the present invention may comprise a strong anionic exchange resin.

An anion exchange chromatography step may be carried out using a buffer, such as, but not limited to, one or more of the buffers described herein. In some embodiments, a Tris buffer may be used in conjunction with an anion exchange chromatography step of a method of the present invention. Thus, a mixture comprising PAP may comprise a Tris buffer. The Tris buffer may comprise Tris-HCl in a concentration from about 1 mM to about 1 M Tris-HCl, such as, but not limited to, a concentration of about 5 mM, 10 mM, 15 mM, 20 mM, 25 mM, 30 mM, 35 mM, etc. The Tris buffer may have a pH of about 7 to about 9, such as, but not limited to, a pH of about 7, 7.5, 8, 8.5, or 9. In some embodiments, a mixture comprising PAP in a Tris buffer having a Tris-HCl concentration of about 10 mM to about 35 mM and a pH from about 7 to about 8 may be contacted with an anionic exchange chromatography resin.

Elution from an anion exchange resin may be achieved by increasing the conductivity of the mobile phase, such as, by adding a salt (e.g., sodium chloride) to a buffer to form an anionic elution buffer. A method of the present invention may comprise contacting an anionic exchange resin with two or more anionic elution buffers that may be the same and/or different. In some embodiments, PAP is eluted from an anionic exchange resin by contacting the anionic exchange resin with an anionic elution buffer. The anionic elution buffer may comprise a salt, such as, but not limited to, sodium chloride, in a concentration from about 5 mM to about 2 M, about 50 mM to about 1 M, about 50 mM to about 100 mM, about 750 mM to about 1.25 M, or about 100 mM to about 300 mM. In some embodiments, the anionic elution buffer comprises a buffer, such as, but not limited to, a Tris buffer, and a salt.

Cation exchange chromatography also relies on charge-charge interactions between the components in the sample, such as, for example, proteins, and the charges immobilized on the anionic chromatography medium. In cation exchange chromatography, the binding ions of the components are positive, and the immobilized functional group of the chromatography medium is negative. Exemplary cation exchange chromatography medium include, but are not limited to, resins, monoliths, or membranes. In some embodiments, a cation exchange chromatography medium is in the form of a column comprising cation exchange chromatography resin.

Strong cation exchange media may comprise a sulfonic acid group, such as sulfopropyl (SP) group, and weak cation exchange media may comprise a weak acid, such as carboxymethyl (CM). Strong cation exchange groups may have a wider pH range compared to weak cation exchangers. Further exemplary functional groups cation exchange chromatography media may comprise include, but are not limited to, carboxylic acid functional groups and sulfonic acid functional groups; examples of such groups include, but are not limited to, sulfonate, carboxylic, carboxymethyl sulfonic acid, sulfoisobutyl, sulfoethyl, carboxyl, sulphopropyl, sulphonyl, sulphoxyethyl, and orthophosphate.

Exemplary cation exchange chromatography media include, but are not limited to, those having a sulfonate based group (e.g., MONO S®, MiniS, Source™ 15S and 30S, SP SEPHAROSE® Fast Flow, and SP SEPHAROSE® High Performance available from GE Healthcare, Germany; TOYOPEARL® SP-650S and SP-650M available from Tosoh Bioscience, Germany; MACRO-PREP® High S available from BioRad, California, USA; Ceramic HYPER D® S, TRISACRYL® M and LS SP and SPHERODEX® LS SP available from Pall Corporation, New York, USA; a sulfoethyl based group (e.g., FRACTOGEL® SE from EMD Millipore, POROS® (S-10 and S-20 available from Applied Biosystems); a sulphopropyl based group (e.g., TSK-GEL® SP 5PW and SP-5PW-HR available from Tosoh, POROS® HS-20 and HS-50 available from Applied Biosystems); a sulfoisobutyl based group (e.g., FRACTOGEL® EMD $SO_3$ available from EMD and ESHMUNO® CPX available from EMD Millipore, Germany); a sulfoxyethyl based group (e.g., SE52, SE53 and EXPRESS-ION® S available from Whatman), a carboxymethyl based group (e.g., CM SEPHAROSE® Fast Flow available from GE Healthcare, HYDROCELL® CM available from Biochrom Labs Inc., MACRO-PREP® CM from BioRad, Ceramic HYPER D® CM, TRISACRYL® M CM, TRISACRYL® LS CM, from Pall Technologies, MATREX® Cellufine C500 and C200 from Millipore, CM52, CM32, CM23 and EXPRESS-ION® C from Whatman, TOYOPEARL® CM-650S, CM-650M and CM-650C from Tosoh); sulfonic and carboxylic acid based groups (e.g. BAKERBOND® Carboxy-Sulfon from J. T. Baker); a carboxylic acid based group (e.g., WP CBX from J. T Baker, DOWEX® MAC-3 from Dow Liquid Separations, Amberlite™ Weak Cation Exchangers, DOWEX® Weak Cation Exchanger, and DIAION® Weak Cation Exchangers from Sigma-Aldrich and FRACTOGEL® EMD $COO^-$ from EMD Millipore); a sulfonic acid based group (e.g., Hydrocell SP from Biochrom Labs Inc., DOWEX® Fine Mesh Strong Acid Cation Matrix from Dow Liquid Separations, UNO SPHERE® S, WP Sulfonic from J. T. Baker, SARTOBIND® S membrane from Sartorius, AMBERLITE® Strong Cation Exchangers, DOWEX® Strong Cation and DIAION® Strong Cation Exchanger from Sigma-Aldrich); and a orthophosphate based group (e.g., PI 1 from Whatman).

Exemplary cation exchange membranes include, but are not limited to, SARTOBIND® S (Sartorius; Edgewood, N.Y.).

Further exemplary cationic exchange chromatography media according to embodiments of the present invention include, but are not limited to, those described in International Publication No. WO 2011/150110 and U.S. Patent Application Publication No. 2013/0317197, the contents of each of which are incorporated herein by reference in their entirety. In some embodiments, a cationic exchange chromatography medium may comprise a hydrophilic polymer matrix, such as, but not limited to, a polyvinylether polymer. The resin may comprise a tentacle structure comprising the hydrophilic polymer matrix with cationic exchange functional groups, such as, but not limited to, sulfoisobutyl functional groups, at the end of the tentacle structure. In some embodiments, a cationic exchange resin in embodiments of the present invention may comprise a sulfoisobutyl functional group. A cationic exchange chromatography medium according to embodiments of the present invention may comprise a strong cationic exchange resin.

A cation exchange chromatography step may be carried out using a buffer, such as, but not limited to, one or more of the buffers described herein. In some embodiments, an acetate buffer, such as, but not limited to a sodium acetate buffer, may be used in conjunction with a cation exchange chromatography step of a method of the present invention. Thus, a mixture comprising PAP may comprise an acetate buffer. The acetate buffer may comprise sodium acetate (NaOAc) in a concentration of about 1 mM to about 1 M NaOAc, such as, but not limited to, a concentration of about 10 mM, 25 mM, 50 mM, 75 mM, etc. The acetate buffer may have a pH of about 3 to about 6, such as, but not limited to, a pH of about 3, 3.5, 4, 4.5, 5, 5.5, or 6. In some embodiments, a mixture comprising PAP in an acetate buffer having a NaOAc concentration of about 25 mM to about 75 mM and a pH from about 4 to about 5 may be contacted with a cationic exchange chromatography resin.

Elution from a cationic exchange resin may be achieved by increasing the conductivity of the mobile phase, such as, by adding a salt (e.g., sodium chloride) to a buffer to form cationic elution buffer. A method of the present invention may comprise contacting a cationic exchange resin with two or more cation elution buffers that may be the same and/or different. In some embodiments, PAP is eluted from a cationic exchange resin by contacting the cationic exchange resin with a cationic elution buffer. The cationic elution buffer may comprise a salt, such as, but not limited to, sodium chloride, in a concentration from about 5 mM to about 2 M, about 50 mM to about 1M, about 50 mM to about 200 mM, about 200 mM to about 600 mM, or about 200 mM to about 400 mM. In some embodiments, the cationic elution buffer comprises a buffer, such as, but not limited to, an acetate buffer, and a salt.

Mixed-mode chromatography medium may be used in a chromatography step of the present invention. Mixed-mode chromatography medium comprise a support or solid phase that is functionalized with two or more different ligands to provide two or more different types of interactions. For example, a mixed-mode chromatography medium may be functionalized with two or more different ligands to provide ion (e.g., cation and/or anion) exchange, hydroxyapatite, affinity, size exclusion, and/or hydrophobic interactions.

Exemplary mixed-mode chromatography resins include, but are not limited to, BAKERBOND® ABx™ (J. T. Baker; Phillipsburg, N.J.); ceramic hydroxyapatite (CHT) type I and II resins and fluoride hydroxyapatite resins (BioRad; Hercules, Calif.); MEP HyperCel™ and MBI HyperCel™ (Pall Corporation; East Hills, N.Y.); Capto™ MMC, Capto™ Adhere, HEA HyperCel™, PPA HyperCel™, CHT™ ceramic hydroxyapatite, Nuvia™ cPrime™; and Bio-Gel HT, Bio-Gel HTP, Biorad, Hercules, Calif. Further exemplary mixed-mode chromatography media include, but are not limited to, those described in U.S. Pat. No. 7,999,085; U.S. Patent Application Publication Nos. 2011/0081700 and 2013/0317197; and International Publication No. WO 2011/150110, the contents of each of which are incorporated herein by reference in their entirety.

According to some embodiments of the present invention, a mixed-mode chromatography medium may comprise a ceramic hydroxyapatite (CHT) or ceramic fluorapatite (CFT) resin of Type I or Type II. The CHT or CFT resin may comprise one or more ionic groups chosen from or selected from the group consisting of $Ca^{2+}$, $PO_4^{3-}$, $OH^-$, and any combination thereof. The resin may have an average particle diameter of about 10, 20, 40, or 80 microns. The choice of hydroxyapatite or fluorapatite, the type, and average particle diameter can be determined by the skilled artisan. In some embodiments, a chromatography step of the present invention comprises a CHT mixed-mode resin. In certain embodiments, the CHT mixed-mode resin is Type II.

A mixed-mode chromatography step may be carried out using a buffer, such as, but not limited to, one or more of the buffers described herein. In some embodiments, a HEPES buffer may be used in conjunction with a mixed-mode chromatography step of a method of the present invention. Thus, a mixture comprising PAP may comprise a HEPES buffer. The HEPES buffer may have a concentration from about 1 mM to about 1 M HEPES, such as, but not limited to, a concentration of about 5 mM, 10 mM, 15 mM, 20 mM, 25 mM, 30 mM, 35 mM, etc. The HEPES buffer may have a pH of about 6 to about 9, such as, but not limited to, a pH of about 6, 6.5, 7, 7.5, 8, 8.5, or 9. In some embodiments, a mixture comprising PAP in a HEPES buffer having a concentration of about 15 mM to about 35 mM HEPES and a pH from about 6.5 to about 7.5 may be contacted with a mixed-mode chromatography resin. The HEPES buffer may comprise a salt optionally in a concentration of about 0.5 mM to about 50 mM or about 1 mM to about 20 mM.

Elution from a mixed-mode chromatography resin may be achieved by methods known to those of skill in the art. A method of the present invention may comprise contacting a mixed-mode chromatography resin with a mixed-mode elution buffer. In some embodiments, PAP may be eluted from a mixed-mode chromatography resin by contacting the mixed-mode chromatography resin with a mixed-mode chromatography elution buffer. The mixed-mode elution buffer may comprise a salt, such as, but not limited to, sodium phosphate, in a concentration from about 0.1 mM to about 1 M, about 1 mM to about 10 mM, or about 1 mM to about 500 mM. In some embodiments, the mixed-mode elution buffer comprises a buffer, such as, but not limited to, an HEPES buffer and salt, such as, but not limited to, sodium phosphate.

Hydrophobic interaction chromatography may be utilized according to some embodiments of the present invention. Hydrophobic interaction chromatography media may comprise a support with a hydrophobic ligand. The support may comprise a base matrix (e.g., cross-linked agarose or synthetic copolymer material) to which hydrophobic ligands (e.g., alkyl or aryl groups) are coupled. "Alkyl" as used herein refers to $C_{1-20}$ inclusive, linear (i.e., "straight-chain"), branched, or cyclic, saturated or at least partially and in some cases fully unsaturated (i.e., alkenyl and alkynyl)hydrocarbon chains. "Aryl" as used herein refers to an aromatic substituent that may be a single aromatic ring, or multiple aromatic rings that are fused together, linked covalently, or linked to a common group, such as, but not limited to, a methylene or ethylene moiety. The term "aryl" specifically encompasses heterocyclic aromatic compounds and substituted aryl compounds, such as, but not limited to aralkyl. The hydrophobic ligand may be available to interact with hydrophobic components, such as, for example, hydrophobic amino acids of a protein. Exemplary hydrophobic ligands or functional groups include, but are not limited to, butyl ether, propyl ether, phenyl, phenyl ether, and any combination thereof.

Exemplary hydrophobic interaction chromatography resins include, but are not limited to, Phenyl SEPHAROSE® 6 Fast Flow; Phenyl SEPHAROSE® High Performance; Phenyl SEPHAROSE® High Sub; Octyl SEPHAROSE® High Performance (Pharmacia LKB Biotechnology, AB, Sweden); FRACTOGEL® EMD Propyl or FRACTOGEL® EMD Phenyl (E. Merck, Germany); MACRO-PREP® Methyl or MACRO-PREP® t-Butyl Supports (Bio-Rad, CA); WP HI-Propyl™ ($C_3$) (J. T. Baker, N.J.); and TOYOPEARL® ether, phenyl or butyl (TosoHaas, Pa.).

A method of the present invention may comprise contacting a hydrophobic interaction chromatography resin comprising cross-linked agarose with a mixture comprising PAP. In some embodiments, the hydrophobic interaction chromatography resin may comprise an aryl functional group, such as, but not limited to, a phenyl functional group.

A hydrophobic interaction chromatography step may be carried out using a buffer, such as, but not limited to, one or more of the buffers described herein. In some embodiments, a phosphate buffer may be used in conjunction with a hydrophobic interaction chromatography step of a method of the present invention. The phosphate buffer may be a sodium phosphate monobasic ($NaH_2PO_4$), sodium phosphate dibasic ($Na_2HPO_4$), potassium phosphate monobasic ($KH_2PO_4$), or a potassium phosphate dibasic ($K_2HPO_4$) buffer. Thus, a mixture comprising PAP may comprise a phosphate buffer. In some embodiments, the phosphate buffer comprises $K_2HPO_4$. The phosphate buffer may have a concentration from about 1 mM to about 3 M $K_2HPO_4$, such as, but not limited to, a concentration of about 1 M to about 3 M, about 1.5 M to about 2.5 M, about 750 mM to about 1.5 M, about 10 mM to about 300 mM, about 400 mM to about 700 mM, or about 100 mM to about 1 M $K_2HPO_4$. The phosphate buffer may have a pH of about 5 to about 8.5, such as, but not limited to, a pH of about 5, 5.5, 6, 6.5, 7, 7.5, 8, or 8.5. In some embodiments, a mixture comprising PAP in a $K_2HPO_4$ buffer having a concentration of about 750 mM to about 2.5 M $K_2HPO_4$ and a pH from about 7 to about 8 may be contacted with a hydrophobic interaction chromatography resin.

Methods for eluting a protein from a hydrophobic interaction chromatography resin are known to those of skill in the art. Hydrophobic interactions may be enhanced or strengthened by buffers with high ionic strength. Therefore, a protein, such as PAP may be eluted from a hydrophobic interaction chromatography resin by reducing the strength of the hydrophobic interaction, such as, but not limited to, by reducing the ionic strength of the mobile phase. In some embodiments, PAP may be eluted from a hydrophobic interaction chromatography resin by contacting the hydrophobic interaction chromatography resin with a hydrophobic interaction chromatography elution buffer. The hydrophobic interaction elution buffer may have a lower ionic strength than the ionic strength of the mixture comprising PAP that contacted the hydrophobic interaction chromatography resin. In some embodiments, the hydrophobic interaction elution buffer comprises a phosphate buffer, such as one or more of those described herein. In certain embodiments, the hydrophobic interaction elution buffer comprises $K_2HPO_4$. The $K_2HPO_4$ buffer may have a concentration from about 50 mM to about 500 mM or about 100 mM to about 300 mM.

A PAP purification method of the present invention may comprise a filtration step, such as, but not limited to, a microfiltration, ultrafiltration/diafiltration, tangential flow filtration, and/or alternating tangential flow filtration step. In some embodiments, a method of the present invention comprises an ultrafiltration/diafiltration step. The ultrafiltration/diafiltration step may be carried out as a continuous diafiltration step, a discontinuous diafiltration step by volume reduction, and/or a discontinuous diafiltration step by sequential dilution. An ultrafiltration/diafiltration step may be used two or more times, such as, but not limited to, three, four, five, or more times, during a method of the present invention. An ultrafiltration/diafiltration step may be used to concentrate a sample, to change the composition of a sample (e.g., to buffer exchange a sample), and/or to remove a component (e.g., a salt) or an impurity in sample. In some embodiments, an ultrafiltration/diafiltration step may be used to change the composition of a sample comprising PAP. The sample may be modified to have a different buffer and/or pH. The sample comprising PAP may be modified to comprise a saline solution, such as but not limited to a phosphate buffered saline solution and/or a 0.9% saline solution. The saline solution may have a pH of about 4 to about 8, such as, but not limited to, a pH of about 4.5 to about 7 or about 5.

Exemplary ultrafiltration/diafiltration materials include, but are not limited to, membranes and filters such as membranes and/or filters comprising cellulose such as regenerated cellulose, polyethersulfone such as modified polyethersulfone, and/or hydrophilic polyvinylidene fluoride. Exemplary commercial ultrafiltration/diafiltration materials include, but are not limited to, PELLICON® 2 microfiltration cassettes with BIOMAX®, ULTRACEL® PLC, and/or DURAPORE® membranes available from EMD Millipore and Allegro™ products from Pall Corporation. The ultrafiltration/diafiltration membrane and/or filter may have a molecular weight cut-off, such as, but not limited to, 10 kDa, 20 kDa, 30 kDa, 40 kDa, 50 kDa, 60 kDa, 70 kDa, 80 kDa, 90 kDa, 100 kDa, 110 kDa, 120 kDa, etc.

A method of the present invention may comprise a viral inactivation step. A viral inactivation step may be carried out as a single step in a method of the present invention or may be carried out multiple times in a method of the present invention. For example, a viral inactivation step may be used two or more times, such as, but not limited to, three, four, five, or more times, during a method of the present invention. Any suitable viral inactivation method may be used in a method of the present invention. Exemplary viral inactivation methods include, but are not limited to, heat inactivation, irradiation such as gamma or UV irradiation, chemical treatment such as with an organic solvent, Tween-80, Triton-X and/or tri(n-butyl)phosphate, filtration such as nanofiltration, precipitation, and those described in International Publication Nos. WO 2008/039021 and WO 2008/098979, the contents of each of which are incorporated herein by referenced in their entirety.

In some embodiments, a method of the present invention comprises a viral inactivation step that may be performed or carried out with a chemical, such as, but not limited to Triton-X. In some embodiments, a method of the present invention comprises a viral inactivation step that may be performed or carried out with a virus removal filter. Exemplary virus removal filters include, but are not limited to, PLANOVA® filters available from Ashai, Glenview, Ill. and VIRESOLVE® available from Millipore, Billerica, Mass. The viral inactivation step may be performed or carried out at any time during a method of the present invention. In some embodiments, a viral inactivation step is performed or carried out after the first chromatography step and/or after the last chromatography step. In certain embodiments, a viral inactivation step is performed or carried out after an anion exchange chromatography step.

A method of the present invention may comprise two or more chromatography steps. A chromatography step of the present invention may be carried out under conditions suitable for at least a portion of PAP to be purified from the mixture. A chromatography step may be carried out at temperature of about 5° C. to about 30° C. In some embodiments, a chromatography step may be carried out at about room temperature, between about 2° C. to about 8° C., or between about 20° C. to about 30° C. Sequential steps in a PAP purification and/or manufacturing method of the present invention may be continuous and/or discontinuous. In some embodiments, a method of the present invention comprises a continuous purification method that optionally may utilize the same flow rate, conductivity, and/or pH for one or more steps.

One or both of the two or more chromatography steps may comprise column chromatography steps. As those skilled in the art will recognize, a chromatography medium, such as a column comprising chromatography resin, may be washed one or more times with an equilibration buffer and the flow-through fraction may be discarded. The equilibration buffer may be the same as or similar to a buffer present in the sample to be loaded onto the column. The column dimensions may be determined by one of skill in the art. For example, as those skilled in the art will recognize, the amount of chromatography resin to be used may depend on the overall protein content of the sample to be applied to the column.

In some embodiments, a chromatography step of a method of the present invention comprises a column having a volume of about 5 mL to about 1 L or more, such as, but not limited to, about 10 mL to about 50 mL, about 40 mL to about 100 mL, about 200 mL to about 750 mL, about 500 mL to about 1 L, or about 50 mL to about 500 mL.

A column chromatography step of the present invention may comprise contacting a sample with a chromatography resin present in a column at any suitable protein load. Thus, the sample may be loaded onto the resin in the column. In some embodiments, the protein load is at least about 0.5 mg PAP/mL chromatography resin. For example, the protein load in may be about 1, 2, 5, 10, 15, 20, 30, 40, 50, 100, 150 or more mg PAP/mL chromatography resin. In certain embodiments, the protein load may be about 1 to about 20 mg PAP/mL chromatography resin.

According to some embodiments of the present invention, a method of the present invention may comprise a method for purifying PAP 100 such as described in FIG. 1. The PAP may be recombinant PAP, such as, but not limited to, recombinant human PAP. The recombinant PAP may be obtained from a cell culture. Thus, the method 100 may comprise the step of clarifying the culture of host cells expressing PAP 110. The clarification step 110 may comprise removing the host cells, such as, but not limited to, mammalian host cells (e.g., human cells, Chinese hamster ovary cells, etc.), from the cell culture medium at the termination of the culture by depth filtration.

After the clarification step 110, an ultrafiltration/diafiltration step 120 may be performed. The ultrafiltration/diafiltration step 120 may be carried out to buffer exchange the clarified harvest. Optionally, the ultrafiltration/diafiltration step 120 may provide a buffer suitable for an anion exchange chromatography step 130. The clarification step 110 and/or the ultrafiltration/diafiltration step 120 may remove cells and cell debris from the cell culture.

An anion exchange chromatography step 130 may then be performed. Alternatively, a method of purifying PAP 100 may start with the anion exchange chromatography step 130 without a prior clarification step 110 and/or ultrafiltration/diafiltration step 120. The anion exchange chromatography step 130 may comprise contacting a sample comprising PAP, such as, but not limited to, the clarified harvest from the clarification step 110 or the sample from the ultrafiltration/diafiltration step 120, with an anion exchange chromatography medium and at least a portion of the PAP may be eluted from the anion exchange chromatography medium. The anion exchange chromatography medium may comprise a strong anion exchange resin, such as, but not limited to, an Eshmuno Q or Q Sepharose chromatography resin. The yield or recovery of PAP in the sample after the anion exchange chromatography step 130 may be at least about 50%, such as, but not limited to, about 61% to about 85%. The host cell protein level in the sample after the anion exchange chromatography step 130 may be reduced by at least 30%, such as, but not limited to, by about 45% to about 62%.

Optionally, a viral inactivation step 135 may be performed or carried out with the eluate from the anion exchange chromatography step 130 (i.e., the sample comprising PAP). The viral inactivation step 135 may optionally comprise a chemical viral inactivation. For example, a chemical viral inactivation may comprise contacting the eluate from the viral inactivation step with 1% Triton X-100 for about 1 to about 2 hours at room temperature.

The eluate from the anion exchange chromatography step 130 or the eluate after the viral inactivation step 135 (i.e., the sample comprising PAP) may be contacted with a cation exchange chromatography medium and at least a portion of the PAP may be eluted from the cation exchange chromatography medium in a cation exchange chromatography step 140. The cation exchange chromatography medium may comprise a strong cation exchange resin, such as, but not limited to, an Eshmuno CPX chromatography resin. The cation exchange chromatography step 140 may be a step gradient process.

In some embodiments, most of the impurities are removed from the sample comprising PAP after the cation exchange chromatography step 140. For example, PAP in the eluate from the cation exchange chromatography step (i.e., the sample comprising PAP) may have a purity of at least about 50%, such as, but not limited to, a purity of at least about 60%, 65%, 70%, 75%, 80%, 85%, 90%, 95% or more. The recovery or yield of PAP in the sample after the cation exchange chromatography step 140 may be at least about 50%, such as, but not limited to, a yield of PAP of at least about 60%, 65%, 70%, 75%, 80%, 85%, 90%, or more or about 65% to about 85%. The host cell protein level in the sample after the cation exchange chromatography step 140 may be reduced by at least 75%, such as, but not limited to, by about 96% to about 99%.

PAP may be further purified after the cation exchange chromatography step 140. Optionally, prior to another chromatography step, an ultrafiltration/diafiltration step 145 may be carried out with the eluate from the cation exchange chromatography step 140 (i.e., the sample comprising PAP). The ultrafiltration/diafiltration step 145 may be carried out to buffer exchange the eluate from the cation exchange chromatography step 140. The ultrafiltration/diafiltration step 145 may provide a buffer suitable for a mixed-mode chromatography step 150. The yield of PAP in the sample after the ultrafiltration/diafiltration step 145 may be at least about 75%, such as, but not limited to, about 87% to about 95%. The host cell protein level in the sample after the ultrafiltration/diafiltration step 145 may be reduced by at least 40%, such as, but not limited to, by about 53% to about 65%.

The eluate from the cation exchange chromatography step 140 or after ultrafiltration/diafiltration step 145 (i.e., the sample comprising PAP) may be contacted with a mixed-mode chromatography medium and at least a portion of the PAP may be eluted from the mixed-mode chromatography medium in the mixed-mode chromatography step 150. The mixed-mode chromatography medium may comprise a ceramic hydroxyapatite. The yield of PAP in the sample after the mixed-mode chromatography step 150 may be at least about 80%, such as, but not limited to, about 95% to about 99%. The host cell protein level in the sample after the mixed-mode chromatography step 150 may be reduced by at least 75%, such as, but not limited to, by about 89% to about 90%. PAP in the eluate from the mixed-mode chromatography step 150 may have a purity of at least about 80%, such as, but not limited to, a purity of at least about 85%, 90%, 95%, 96%, 97%, 98%, 98.5%, 99%, 99.5%, or more.

The eluate from the mixed-mode chromatography step 150 (i.e., the sample comprising PAP) may then be contacted with a hydrophobic interaction chromatography medium and at least a portion of the PAP may be eluted from the hydrophobic interaction chromatography in a hydrophobic interaction chromatography step 160. The hydrophobic interaction chromatography step 160 may comprise a step gradient process. The hydrophobic interaction chromatography medium may comprise an aryl functional group, such as, but not limited to, phenyl. The yield of PAP in the sample after the hydrophobic interaction chromatography step 160 may be at least about 60%, such as, but not limited to, about 78% to about 87%. The host cell protein level in the sample after the hydrophobic interaction chromatography step 160 may be reduced by at least 80%, such as, but not limited to, by about 90% to about 99%.

A viral inactivation step 165 may be performed or carried out with the eluate from the hydrophobic interaction chromatography step 160 (i.e., the sample comprising PAP). The viral inactivation step 165 may optionally comprise a filtration viral inactivation. For example, a filtration viral inactivation may comprise filtering, such as, but not limited to, nanofiltering, the eluate from the hydrophobic interaction chromatography step 160. The yield of PAP in the sample after the viral inactivation step 165 may be at least about 90%, such as, but not limited to, about 96% to about 98%. The host cell protein level in the sample after the viral inactivation step 165 may be reduced by at least 80%, such as, but not limited to, by about 90% to about 99%.

An ultrafiltration/diafiltration step 170 may be performed or carried out with the eluate from the viral inactivation step 165 (i.e., the sample comprising PAP). The ultrafiltration/diafiltration step 170 may be carried out to buffer exchange the sample comprising PAP. Optionally, the ultrafiltration/diafiltration step 170 may provide a buffer suitable for a composition comprising PAP, such as, but not limited to, a pharmaceutical composition, or for a medicament comprising PAP. In some embodiments, the ultrafiltration/diafiltration step 170 may be used to provide PAP in a saline solution, optionally a 0.9% saline solution or phosphate buffered saline solution. The yield of PAP in the sample after the ultrafiltration/diafiltration step 170 may be at least about 70%, such as, but not limited to, about 81% to about 91%. The host cell protein level in the sample after the ultrafiltration/diafiltration step 170 may be reduced by at least 50%, such as, but not limited to, by about 63% to about 64%.

A sterile filtration step 180 may be carried out after one or more steps in the method for purifying PAP 100. For example, sterile filtration steps 180a-180j may be performed or carried out after each of the steps in the method 100.

The method 100 advantageously provides PAP of a high purity and activity with low host cell contaminants. The method of purifying PAP 100 provides a substantially purified PAP. For example, in some embodiments, the final protein purity of PAP after method 100 is at least about 50%, such as, but not limited to, a purity of at least about 60%, 65%, 70%, 75%, 80%, 85%, 90%, 95% or more. In some embodiments, the method 100 provides PAP having a purity of least about 98%, such as, but not limited to, a purity of at least about 98.5%, 99%, 99.5%, or more. The method 100, in some embodiments, provides a host cell protein concentration of less than about 100 ppm and/or a host cell rDNA concentration of less than about 100 pg host cell rDNA per mg PAP. In some embodiments, PAP after the method 100 has a specific activity of about 200 to about 500 units/mg PAP. Thus, in some embodiments, after the method of purifying PAP 100, the sample comprising PAP has a PAP purity of at least about 98%, a host cell protein concentration of less than about 100 ppm, a host cell rDNA concentration of less than about 100 pg host cell rDNA per mg PAP, and/or a specific activity of about 200 to about 500 units/mg PAP.

According to some embodiments of the present invention, a purified PAP may be obtained according to a purification method of the present invention. The purified PAP may be isolated. "Isolated" as used herein refers to PAP that has been separated, removed, recovered, and/or the like from one or more components in its natural environment. In some embodiments the isolated PAP may have a purity of greater than about 60%, a host cell protein content of less than about 100 ng/mg PAP, and/or a host cell DNA content of less than about 100 pg/mg PAP. In certain embodiments, the PAP may have a purity of greater than about 90%; in further embodiments, greater than about 95%; and in yet further embodiments, greater than about 95%.

PAP according to embodiments of the present invention may have a specific activity of at least about 20% compared to the specific activity of native PAP from which the PAP is obtained or derived. In some embodiments, PAP has a specific activity of at least about 30%, 40%, 50%, 60%, 70%, 80%, 90% or more compared to the specific activity of native PAP from which the PAP is obtained or derived. Methods of assaying and/or quantifying measures of protein and protein activity and substrate specificity ($k_{cat}/K_m$) are well known to those of skill in the art and include, but are not limited to, those described in U.S. Patent Application Publication No. 2013/0317197, the contents of which are incorporated herein by reference in its entirety. In some embodiments, PAP according to embodiments of the present invention, such as a purified human PAP, may have a specific activity of about 100 to about 1000 units/mg PAP, such as, but not limited to, about 200 to about 500 units/mg PAP or about 250 to about 350 units/mg PAP. In solution, PAP may have an activity of about 1,000 to about 8,000 units/mL, such as, but not limited to, about 3,000 to about 6,000 units/mL or about 4,000 to about 5,000 units/mL.

Provided herein are compositions comprising PAP. The PAP may be obtained according to a purification and/or manufacturing method of the present invention. The PAP may have a purity of greater than about 60% prior to its addition to the composition, a host cell protein content of less than about 100 ng/mg PAP, and/or a host cell DNA content of less than about 100 pg/mg PAP. As those of skill in the art will recognize, after addition to a composition the purity of PAP may decrease if other components are present in the composition. In some embodiments, the PAP has a purity of greater than about 75%; in certain embodiments, greater than about 90%; in further embodiments, greater than about 95%; and in yet further embodiments, greater than about 95% prior to the addition to the composition.

A composition comprising PAP according to embodiments of the present invention may comprise PAP in a range of about 10 units/mL to about 20,000 units/mL. In some embodiments, PAP may be present a composition of the present invention in a range of about 100 units/L to about 10,000 units/mL, about 1,000 units/L to about 10,000 units/mL, about 4,000 units/L to about 5,000 units/mL, about 2,500 units/L to about 7,500 units/mL, about 900 units/L to about 4,000 units/mL, about 500 units/L to about 4,500 units/mL, about 500 units/L to about 1,000 units/mL, about 700 units/L to about 1,100 units/mL, about 50 units/L to about 500 units/mL, or about 100 units/L to about 500 units/mL.

A pharmaceutical composition may be provided according to some embodiments of the present invention. In some embodiments, a pharmaceutical composition of the present invention may comprise PAP and a pharmaceutically acceptable carrier. The PAP may be obtained according to a purification and/or manufacturing method of the present invention. Any suitable pharmaceutically acceptable carrier known to those of skill in the art may be used in a pharmaceutical composition of the present invention. In some embodiments, the pharmaceutical composition comprises PAP and saline, such as, but not limited to, 0.9% saline and/or phosphate buffered saline. The PAP in the pharmaceutical composition may have a purity of greater than about 60% prior to addition to the pharmaceutical composition, a host cell protein content of less than about 100 ng/mg PAP, and/or a host cell DNA content of less than about 100 pg/mg PAP. In some embodiments, the PAP has a purity of greater than about 75%; in certain embodiments, greater than about 90%; in further embodiments, greater than about 95%; and in yet further embodiments, greater than about 95% prior to the addition to the pharmaceutical composition.

A pharmaceutical composition comprising PAP according to embodiments of the present invention may comprise PAP in a range of about 10 units/mL to about 20,000 units/mL. In some embodiments, PAP may be present a pharmaceutical composition of the present invention in a range of about 100 units/L to about 10,000 units/mL, about 1,000 units/L to about 10,000 units/mL, about 4,000 units/L to about 5,000 units/mL, about 2,500 units/L to about 7,500 units/mL, about 900 units/L to about 4,000 units/mL, about 500 units/L to about 4,500 units/mL, about 500 units/L to about 1,000 units/mL, about 700 units/L to about 1,100 units/mL, about 50 units/L to about 500 units/mL, or about 100 units/L to about 500 units/mL.

A medicament may be provided according to some embodiments of the present invention. In some embodiments, a medicament of the present invention may comprise PAP and an acceptable carrier. The PAP may be obtained according to a purification and/or manufacturing method of the present invention. Any suitable carrier known to those of skill in the art may be used in a medicament of the present invention. In some embodiments, the medicament comprises PAP and saline, such as, but not limited to, 0.9% saline and/or phosphate buffered saline. The PAP in the medicament may have a purity of greater than about 60% prior to formulation or addition to the medicament, a host cell protein content of less than about 100 ng/mg PAP, and/or a host cell DNA content of less than about 100 pg/mg PAP. In some embodiments, the PAP has a purity of greater than about 75%; in certain embodiments, greater than about 90%; in further embodiments, greater than about 95%; and in yet further embodiments, greater than about 95% prior to the addition to or the formulation of the medicament.

A medicament comprising PAP according to embodiments of the present invention may comprise PAP in a range of about 10 units/mL to about 20,000 units/mL. In some embodiments, PAP may be present a medicament of the present invention in a range of about 100 units/L to about 10,000 units/mL, about 1,000 units/L to about 10,000 units/mL, about 4,000 units/L to about 5,000 units/mL, about 2,500 units/L to about 7,500 units/mL, about 900 units/L to about 4,000 units/mL, about 500 units/L to about 4,500 units/mL, about 500 units/L to about 1,000 units/mL, about 700 units/L to about 1,100 units/mL, about 50 units/L to about 500 units/mL, or about 100 units/L to about 500 units/mL.

"Pharmaceutically acceptable carrier" and "acceptable carrier" as used herein refer to a carrier that is compatible with other ingredients in the pharmaceutical composition or medicament and that is not harmful or deleterious to the subject, i.e., the carrier can be administered to a subject without causing any undesirable biological effects such as toxicity. The carrier may be a solid or a liquid, or both, and may be formulated with a composition of this invention as a unit-dose formulation, which may contain the compound (i.e., PAP) in an amount of about 0.01% or 0.5% to about 95% or 99% by weight of the composition.

The compositions and medicaments (i.e., formulations) of the invention may optionally comprise medicinal agents, pharmaceutical agents, carriers, adjuvants, dispersing agents, diluents, and the like.

The compounds of the invention may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the compound (including the physiologically acceptable salts thereof) is typically admixed with, inter alia, an acceptable carrier. One or more compounds may be incorporated in the formulations of the invention, which may be prepared by any of the well-known techniques of pharmacy.

The formulations of the invention include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, into the brain for delivery to the central nervous system, into the pancreas, or into a tumor or the tissue surrounding a tumor). The most suitable route in any given case will depend on the nature and severity of the condition being treated and on the nature of the particular compound which is being used.

In some embodiments, a pharmaceutical composition and/or medicament of the present invention may be suitable for intrathecal delivery and/or may be administered to a patient in need thereof intrathecally. In certain embodiments, a pharmaceutical composition and/or medicament of the present invention may be administered by intrathecal injection and/or by a pump providing intrathecal delivery.

For injection, the carrier will typically be a liquid, such as sterile pyrogen-free water, pyrogen-free phosphate-buffered saline solution, bacteriostatic water, or CREMOPHOR® EL[R] (BASF, Parsippany, N.J.). For other methods of administration, the carrier may be either solid or liquid.

For oral administration, the compound may be administered in solid dosage forms, such as capsules, tablets, and powders, or in liquid dosage forms, such as elixirs, syrups, and suspensions. Compounds may be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents may be used to make compressed tablets. Both tablets and capsules may be manufactured as sustained release products to provide for continuous release of medication over a period of hours. Compressed tablets may be sugar coated or film coated to mask any unpleasant taste and protect the tablet from the atmosphere, or enteric-coated for selective disintegration in the gastrointestinal tract. Liquid dosage forms for oral administration may contain coloring and flavoring to increase patient acceptance.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations suitable for parenteral administration comprise sterile aqueous and non-aqueous injection solutions of the compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use.

Extemporaneous injection solutions and suspensions may be prepared from sterile powders, granules and tablets of the kind previously described. For example, in one aspect of the present invention, there is provided an injectable, stable, sterile composition comprising a compound of the invention, in a unit dosage form in a sealed container. The compound or salt may be provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is pharmaceutically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, Tyle, *Pharm. Res.* 3:318 (1986), which is incorporated by reference herein in its entirety) and typically take the form of an optionally buffered aqueous solution of the compound. Suitable formulations comprise citrate or bis/tris buffer (pH 6) or ethanol/water and contain from 0.1 to 0.2M of the compound.

The compound may alternatively be formulated for nasal administration or otherwise administered to the lungs of a subject by any suitable means, e.g., administered by an aerosol suspension of respirable particles comprising the compound, which the subject inhales. The respirable particles may be liquid or solid. The term "aerosol" includes any gas-borne suspended phase, which is capable of being inhaled into the bronchioles or nasal passages. Specifically, aerosol includes a gas-borne suspension of droplets, as may be produced in a metered dose inhaler or nebulizer, or in a mist sprayer. Aerosol also includes a dry powder composition suspended in air or other carrier gas, which may be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the compound may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compound may likewise be produced with any solid particulate medicament aerosol generator, by techniques known in the pharmaceutical art.

Alternatively, one may administer the compound in a local rather than systemic manner, for example, in a depot or sustained-release formulation.

A composition, pharmaceutical composition, and/or medicament of the present invention may comprise a therapeutically effective amount of PAP and/or may be formulated to administer a therapeutically effective amount of PAP. As used herein, the term "therapeutically effective amount" refers to an amount of PAP according to embodiments of the present invention that elicits a therapeutically useful response in a subject. Those skilled in the art will appreciate that the therapeutic effects need not be complete or curative, as long as some benefit is provided to the subject. In particular embodiments of the present invention, a therapeutically effective amount of PAP of the present invention may be administered intrathecally. In some embodiments, intrathecal administration of a composition, pharmaceutical composition, and/or medicament of the present invention may deliver PAP in an amount of about 50 units/mL to about 1,000 units/mL or about 100 units/mL to about 500 units/mL.

According to some embodiments of the present invention, a composition, pharmaceutical composition, and/or medicament of the present invention may be administered to a subject and/or used to treat a subject. Exemplary methods of administering and/or treating a subject include, but are not limited to, those described in U.S. Patent No. 2010/0266569, which is incorporated herein by reference in its entirety. For example, in some embodiments, a method of the present invention may comprise administering a composition, pharmaceutical composition, and/or medicament according to embodiments of the present invention to treat pain in a subject, cystic fibrosis in a subject, and/or a disorder characterized at least in part by an excess of lysophosphatidic acid in subject. In some embodiments, a method of the present invention may comprise administering a composition, pharmaceutical composition, and/or medicament according to embodiments of the present invention to a subject to generate and/or increase the concentration of adenosine in the subject. In certain embodiments, a method of the present invention may be used to generate and/or increase the level or concentration of adenosine in a lung of a subject.

The present invention finds use in both veterinary and medical applications. Suitable subjects of the present invention include, but are not limited to avians and mammals. The term "avian" as used herein includes, but is not limited to, chickens, ducks, geese, quail, turkeys, pheasants, ratites (e.g., ostrich), parrots, parakeets, macaws, cockatiels, canaries, finches, and birds in ovo. The term "mammal" as used herein includes, but is not limited to, primates (e.g., simians and humans), non-human primates (e.g., monkeys, baboons, chimpanzees, gorillas), bovines, ovines, caprines, ungulates, porcines, equines, felines, canines, lagomorphs, pinnipeds, rodents (e.g., rats, hamsters, and mice), and mammals in utero. In some embodiments of the present invention the subject is a mammal and in certain embodiments the subject is a human Human subjects include both males and females of all ages including fetal, neonatal, infant, juvenile, adolescent, adult, and geriatric subjects as well as pregnant subjects.

In certain embodiments of the present invention, the subject is "in need of" a method of the present invention, e.g., the subject is in pain, it is believed that the subject will be in pain, and/or it is believed that the subject is in pain. Further embodiments of the present invention may provide a method of producing recombinant PAP. The recombinant PAP may be human PAP and/or bovine PAP. In some embodiments, a method of producing PAP may comprise culturing or growing a cell, such as, but not limited to, a mammalian cell, expressing a recombinant PAP, and maintaining the cells to thereby produce PAP. The cells may thus be host cells expressing recombinant PAP (i.e., PAP host cells). In some embodiments, a plurality of PAP host cells may be cultured.

In some embodiments, the cells are human cells or Chinese hamster ovary cells. In certain embodiments, the cells stably express soluble PAP. Methods and vectors for genetically engineering cells and/or cell lines to express a protein of interest are well known to those skilled in the art; for example, various techniques are illustrated in *Current Protocols in Molecular Biology*, Ausubel et al., eds. (Wiley & Sons, New York, 1988, and quarterly updates) and Sambrook et al., *Molecular Cloning: A Laboratory Manual* (Cold Spring Laboratory Press, 1989) and are described in U.S. Pat. Nos. 7,091,004 and 8,512,983, the contents of each of which are incorporated herein by reference in their entirety.

The cells may be cultured or grown in any suitable cell culture medium. In some embodiments, the cells may be cultured in a defined serum-free base medium during a growth phase. The base medium may be animal component free. Exemplary defined serum-free base media include, but are not limited to, those described in Table 17 and those described in U.S. Pat. No. 7,091,004, the contents of which are incorporated herein by reference in its entirety.

One or more nutrients and/or supplements may be added to the base medium. Exemplary nutrients and/or supplements include, but are not limited to, vitamins, minerals, salts, growth factors, carbohydrates, proteins, serums, amino acids, attachment factors, cytokines, hormones, antibiotics, therapeutic agents, buffers, L-glutamine, sodium hypoxanthine, thymidine, etc. In some embodiments, the base medium comprises at least one of L-glutamine, sodium hypoxanthine, and thymidine.

The method of producing PAP may comprise maintaining the cells in the base medium during a production phase. The cells may be maintained by supplementing the base medium with a defined serum-free feed medium. The feed medium may be animal component free. Exemplary defined serum-free base media include, but are not limited to, those described in Table 18.

The culturing and/or maintaining step of a method of the present invention may be carried out in a sterile environment using equipment and methods known to those of skill in the art. In some embodiments, the temperature of the culturing and/or maintaining environment may be about 25° C. to about 40° C., such as, but not limited to, about 30° C. to about 40°

C. or about 35° C. to about 40° C. In particular embodiments, the temperature of the culturing and/or maintaining environment may be about 37° C.

The culturing and/or maintaining environment may be at atmospheric pressure, reduced pressure (e.g., vacuumized pressure), high pressure, and/or any combination thereof. In particular embodiments, the pressure of the culturing and/or maintaining step environment may be at atmospheric pressure.

In some embodiments, the culturing and/or maintaining step may be carried out in an atmosphere of about 1% to about 20% carbon dioxide ($CO_2$), such as, but not limited to, about 1% to about 10% or about 1% and about 10% $CO_2$. In certain embodiments, the culturing and/or maintaining step may be carried out in an atmosphere of about 5% $CO_2$. Other gases, such as, but not limited to, nitrogen and/or oxygen, may be added to the culturing and/or maintaining atmosphere. In some embodiments, one or more gases may be used to obtain and/or maintain the desired atmosphere (e.g., to maintain the desired oxygen and/or carbon dioxide levels).

The cell culture may have a dissolved oxygen content of at least about 10%, such as, but not limited to, at least about 20%, 30%, 40%, 50%, 60%, 70%, 80%, 90% or more. In some embodiments, the cell culture may have a dissolved oxygen content of at least about 50%. The cell culture may have a pH of about 5 to about 9, such as, but not limited to, about 6 to about 8 or about 7.

According to some embodiments, the cell culture may be maintained and/or kept at a temperature of about 37° C., have a pH of about 7.0, and/or have a dissolved oxygen content of at least about 50%.

The supplementing step may be carried out at a cell density of at least about $1.0\times10^6$, such as, but not limited to, at least about $2.0\times10^6$, $3.0\times10^6$, $4.0\times10^6$, $5.0\times10^6$, $6.0\times10^6$, $7.0\times10^6$, $8.0\times10^6$, $9.0\times10^6$, or more. In some embodiments, the supplementing step may be carried out at a cell density of about $6.0\times10^6$.

A supplementing step may carried out and/or repeated as needed during a maintaining step. In some embodiments, the supplementing step may be carried out and/or repeated two or more times during the maintaining step, such as, but not limited to, three, four, five, six, seven, eight, or more times during a maintaining step. A supplementing step may occur about every 6 hours, 12 hours, or 24 hours or about every other day, every 3, 4, 5, or 6 days, or about once a week. In some embodiments, a supplementing step may be carried out and/or repeated about every other day.

A supplementing step may comprise adding the feed medium as a bolus at a rate of at least about 1% of the initial culture volume per feed addition. In some embodiments, the rate may be about 1%, 2%, 3%, 4%, 5%, 6%, 7%, 8%, 9%, 10%, 11%, 12%, 13%, 14%, 15%, 16%, 17%, 18%, 19%, 20%, or more of the initial culture volume per feed addition.

In some embodiments, a maintaining step comprises supplementing the base medium with a sugar, such as, but not limited to, glucose. The sugar may be added to the base medium to maintain a desired sugar concentration, such as, but not limited to, a sugar concentration of at least about 1 g sugar per L. In some embodiments, a sugar is added to the base medium to maintain a sugar concentration of about 1 g to about 20 g sugar per L or about 3 g to about 6 g of sugar per L. In certain embodiments, the sugar may be glucose.

The cell culture comprising PAP may have PAP titers or a PAP concentration of at least about 50 mg/L. In some embodiments, the PAP titers may be at least about 100 mg/L or more, such as, but not limited to, about 150, 200, 250, 300, 350, 400 or more mg/L. In certain embodiments, the cell culture comprising PAP may have PAP titers of about 200 mg/L to about 300 mg/L. As those of skill in the art will recognize, PAP titers and/or the concentration of PAP may be measured differently and/or may provide different values when the PAP is secretory compared to transmembrane.

PAP may be obtained from the cell culture according to methods known to those of skill in the art. Different methods may be used if the desired PAP is secretory PAP or transmembrane PAP. For example, when the PAP is secretory, the cell culture medium may be collected and PAP may be recovered or isolated from the cell culture medium. In some embodiments, secretory PAP produced according to a method of present invention is separated from the cell culture medium according to embodiments of the present invention. Secretory PAP may also be recovered from host cell lysates. Transmembrane PAP may be obtained by releasing PAP from the membrane, which may be done by using a suitable detergent solution (e.g., Triton-X 100) or by enzymatic cleavage.

The present invention is explained in greater detail in the following non-limiting Examples.

EXAMPLES

Example 1

Clarified harvests from 5 L bioreactors (Brx 8 and 9) were prepared from cultures of Chinese hamster ovary (CHO) cells expressing human, secretory PAP (hPAP). Brx 8 and 9 contained cell culture of approximately 4 L of CHO harvest, and were each processed for clarification, buffer exchange, and concentration. The detailed steps are:

1. The harvested CHO cells were clarified using a single Millipore POD depth filter, COHC, 0.054 $m^2$, at a ratio of 83 liters of harvest/$m^2$ of depth filter area.
2. The clarified harvests were then concentrated to 0.45 and 0.46 L for Brx 8 and 9, respectively.
3. Each clarified harvest was buffer exchanged versus 10 volumes of 20 mM Tris-HCl, pH 7.5 by ultra-filtration/diafiltration (UF/DF) using a 0.1 $m^2$ Pellicon 2 mini 30 K PES membrane.
4. The concentrated sample was sterile filtered using 0.22 µm Steripak GP 20 filter.

The percentage recovery of hPAP from both bioreactor samples for the clarification and UF/DF steps was approximately 100% by analyzing the hPAP activity. The hPAP was concentrated and buffer exchanged to appropriate conditions (20 mM Tris, pH 7.5) for further purification process steps.

Example 2

Approximately 428 mL (Brx 8) and approximately 455 mL (Brx 9) of clarified harvest of hPAP (total ~1,150 mg hPAP for Brx 8, and ~793 mg of hPAP for Brx 9) was loaded onto a 250 mL-ESHMUNO® Q column. The ESHMUNO® Q column was previously sanitized with 1 N NaOH and equilibrated with 5 column volumes (CV) of 25 mM Tris-HCl, pH 7.5. After loading the sample, the column was washed with 8 CV of 25 mM Tris-HCl, 0.085M NaCl, pH 7.5. Then, proteins containing hPAP were eluted by using 25 mM Tris-HCl, 0.21 M NaCl, pH 7.5 (8 CV for Brx 8 and 5 CV for Brx 9). Three CV of 25 mM Tris-HCl, 1 M NaCl, pH 7.5 was used to strip off proteins bound tightly to the column. All fractions were collected and the flow rate was 50 mL/min or a linear flow rate of 150 cm/hour. Load, flow through, wash, and elution samples were analyzed by SDS-PAGE, hPAP activity assay, HCP, and rDNA analysis.

Approximately 61% (Brx 8) and 85% (Brx 9) of the loaded hPAP activity units were recovered in the elution peak fractions. Less than 5% hPAP activity units were recovered in the flow through fractions (Tables 1 and 2). No significant activity was recovered in the wash or strip fractions. There was about 62% (Brx 8) and 45% (Brx 9) host cell protein (HCP) reduction in the elution peak fractions with the final HCP concentration of 4,948,389 (Brx 8) and 6,772,213 (Brx 9) ng of HCP/mg of hPAP. The rDNA remained in the elution was 2.1 (Brx 8) and 3.8 (Brx 9) pg/mg of hPAP. While not wishing to be bound to any particular theory, the SDS-PAGE analysis of the chromatographic fractions suggests that the hPAP has been captured and the data suggest that Eshmuno Q anion chromatography using step gradient elution at neutral pH works well for the initial purification of hPAP from CHO cell culture.

was previously sanitized with 1 N NaOH and equilibrated with 5 CV of 25 mM NaOAc, pH 4.5. After loading the sample, the column was washed with 12 CV of 50 mM NaOAc, 0.15 M NaCl, pH 4.5. Then, proteins containing hPAP were eluted with 5 CV of 50 mM NaOAc, 0.29 M NaCl, pH 4.5. Five CV of 50 mM NaOAc, 1 M NaCl, pH 4.5 was used to strip off proteins bound tightly to the column. All fractions were collected at a flow rate of 20 mL/min or a linear flow rate of 150 cm/hour. Load, flow through, wash, and elution samples were analyzed by SDS-PAGE, hPAP activity assay, HCP, and rDNA analysis. A prior experiment demonstrated that these conditions removed the majority of protein impurities with a 65-85% hPAP recovery.

Approximately 85% (Brx 8) and 65% (Brx 9) of the loaded hPAP activity units were recovered in the elution peak fractions (Tables 3 and 4), consistent with the prior experiment.

TABLE 1

ESHMUNO ® Q chromatography (Brx 8)

| Fractions | Titer (mg/L) | Volume (mL) | Total enzyme units | % hPAP recovery | HCP Avg. ng/mL | HCP Total ng | HCP Avg. ng/mg | % HCP reduction | rDNA pg/mg |
|---|---|---|---|---|---|---|---|---|---|
| Load | 2687 | 428 | 1150 | 100% | $2.2 \times 10^7$ | $9.3 \times 10^9$ | $8.1 \times 10^6$ | N/A | N/A |
| Flow through | 72 | 600 | 43 | 3.8% | $1.9 \times 10^6$ | $1.2 \times 10^9$ | $2.7 \times 10^7$ | 87% | N/A |
| Elution | 775 | 910 | 705 | 61% | $3.8 \times 10^6$ | $3.5 \times 10^9$ | $4.9 \times 10^6$ | 62% | 2.1 |

TABLE 2

ESHMUNO ® Q chromatography (Brx 9)

| Fractions | Titer (mg/L) | Volume (mL) | Total enzyme units | % hPAP recovery | HCP Avg. ng/mL | HCP Total ng | HCP Avg. ng/mg | % HCP reduction | rDNA pg/mg |
|---|---|---|---|---|---|---|---|---|---|
| Load | 1743 | 455 | 793 | 100% | $1.8 \times 10^7$ | $8.4 \times 10^9$ | $1.1 \times 10^7$ | N/A | N/A |
| Flow through | 63 | 600 | 38 | 5% | $2.2 \times 10^6$ | $1.3 \times 10^9$ | $3.6 \times 10^7$ | 84% | N/A |
| Elution | 1594 | 425 | 678 | 85% | $1.1 \times 10^7$ | $4.6 \times 10^9$ | $6.8 \times 10^6$ | 45% | 3.8 |

Example 3

Cation exchange chromatography chromatography was used to further purify hPAP and remove protein impurities, HCP and rDNA for hPAP previously purified on an anion exchange chromatography resin from Brx 8 and 9.

Approximately 900 mL (Brx 8) and approximately 345 mL (Brx 9) of eluate from a ESHMUNO® Q column (total ~550 mg hPAP for Brx 8, and ~398 mg of hPAP for Brx 9) was diluted 5 fold with 25 mM NaOAc, pH 4.5 and then treated with 1% Triton X-100 for viral inactivation for 1 hour at room temperature. The samples were then loaded onto a 80 mL-ESHMUNO® CPX column. The ESHMUNO® CPX column No significant activity was recovered in the flow through, wash or strip fraction. There was about 99% (Brx 8) and 96% (Brx 9) HCP reduction in the elution peak fractions with the final HCP concentration of 790,761 (Brx 8) and 769,040 (Brx 9) ng of HCP/mg of hPAP. The rDNA remained in the elution was 5.8 (Brx 8) and 4.6 (Brx 9) pg/mg of hPAP. The SDS-PAGE analysis of the chromatographic fractions suggests the hPAP has been captured and further purified. While not wishing to be bound to any particular theory, the data suggest ESHMUNO® CPX cation chromatography using step salt gradient elution at acidic pH works well for further purification of hPAP.

TABLE 3

ESHMUNO ® CPX chromatography (Brx 8)

| Fractions | Titer (mg/L) | Volume (mL) | Total enzyme units | % hPAP recovery | HCP Avg. ng/mL | HCP Total ng | HCP Avg. ng/mg | % HCP reduction | rDNA pg/mg |
|---|---|---|---|---|---|---|---|---|---|
| Load | 610 | 900 | 550 | 100% | $6.6 \times 10^6$ | $6.0 \times 10^9$ | $1.1 \times 10^7$ | N/A | N/A |
| Elution | 1535 | 305 | 468 | 85% | $2.8 \times 10^5$ | $8.5 \times 10^7$ | $7.9 \times 10^5$ | 99% | 5.8 |

TABLE 4

ESHMUNO ® CPX chromatography (Brx 9)

| Fractions | Titer (mg/L) | Volume (mL) | Total enzyme units | % hPAP recovery | HCP Avg. ng/mL | HCP Total ng | HCP Avg. ng/mg | % HCP reduction | rDNA pg/mg |
|---|---|---|---|---|---|---|---|---|---|
| Load | 1154 | 345 | 398 | 100% | $1.4 \times 10^7$ | $4.8 \times 10^9$ | $1.2 \times 10^7$ | N/A | N/A |
| Elution | 867 | 300 | 260 | 65% | $6.7 \times 10^5$ | $2.0 \times 10^8$ | $7.7 \times 10^5$ | 96% | 4.6 |

Example 4

Ceramic Hydroxyapatite (CHT) Type II, 40 μm, mixed-mode chromatography was used to further purify hPAP. However, prior to the mixed-mode chromatography, elutions from the Eshmuno CPX Chromatography were buffer exchanged to 25 mM Hepes, 5 mM NaPO$_4$, pH 7.0 using a regenerated cellulose 30 kDa membrane. A sample of load, permeate, and retentate were saved and submitted for hPAP activity and HCP analysis.

Approximately 87% (Brx 8) and 95% (Brx 9) of the loaded hPAP activity units were recovered in the retentate fractions (Tables 5 and 6). No significant activity was recovered in the permeate fractions. There was about 65% (Brx 8) and 53% (Brx 9) HCP reduction in retentate fractions with the final HCP concentration of 42,214 (Brx 8) and 155,533 (Brx 9) ng/mg of hPAP. While not wishing to be bound by any particular theory, the results show that a UF/DF step is efficient in buffer exchange for the next step purification as well as removing of HCP.

320 mL (Brx 8) and 300 mL (Brx 9) of retentate from UF/DF in 25 mM HEPES, 5 mM NaPO$_4$, pH 7.0 (total ~435 mg for Brx 8 and 279 mg for Brx 9 of hPAP) was loaded onto a 31 mL (Brx 8) or a 17 mL (Brx 9) CHT Type II column. The CHT Type II column was previously sanitized with 1 N NaOH and equilibrated with 5 CV of Buffer A (25 mM HEPES, 5 mM NaPO$_4$, pH 7.0). After loading the sample, the column was washed with 8 CV of buffer A. A 20 CV gradient of 0-100% of Buffer B (25 mM HEPES, 150 mM Sodium Phosphate, pH 7.0) was used to elute protein bound to the column. Four CV of 100% Buffer B was used to strip off protein bound tightly to the column. All the fractions were collected and the flow rate was 10 mL/min (Brx 8) and 5 mL/min (Brx 9) or a linear flow rate of 150 cm/hour. Load, flow through plus wash, and elution samples were analyzed by SDS-PAGE, hPAP activity assay, HCP, and rDNA analysis.

Approximately 95% (Brx 8) and 99% (Brx 9) of the loaded hPAP activity units were recovered in the flow through plus wash fractions and no significant amount of hPAP was recovered in the elution peak fractions (Tables 7 and 8). There was about 90% (Brx 8) and 89% (Brx 9) HCP reduction in the flow through plus wash fractions with the final HCP concentration of 3,691 and 15,318 ng of HCP/mg of hPAP. The rDNA remained in the flow through plus wash fractions was 6.6 (Brx 8) and 5.8 (Brx 9) pg/mg of hPAP. The SDS-PAGE analysis of the chromatographic fractions shows highly purified hPAP in the flow through plus wash fractions with no detectable contaminant protein on the gel. While not wishing to be bound by any particular theory, the data suggest that the CHT type II chromatography is capable of removing protein impurities and rDNA, and isolating highly pure hPAP.

TABLE 5

Intermediate UF/DF (Brx 8)

| Fractions | Titer (mg/L) | Volume (mL) | Total enzyme units | % hPAP recovery | HCP Avg. ng/mL | HCP Total ng | HCP Avg. ng/mg | % HCP reduction | rDNA pg/mg |
|---|---|---|---|---|---|---|---|---|---|
| Load | 1511 | 300 | 453 | 100% | $1.6 \times 10^5$ | $4.8 \times 10^7$ | $1.0 \times 10^5$ | N/A | ND |
| Retentate | 1202 | 328 | 394 | 87% | $5.1 \times 10^4$ | $1.7 \times 10^7$ | $4.2 \times 10^4$ | 65% | ND |

TABLE 6

Intermediate UF/DF (Brx 9)

| Fractions | Titer (mg/L) | Volume (mL) | Total enzyme units | % hPAP recovery | HCP Avg. ng/mL | HCP Total ng | HCP Avg. ng/mg | % HCP reduction | rDNA pg/mg |
|---|---|---|---|---|---|---|---|---|---|
| Load | 1000 | 300 | 300 | 100% | $3.1 \times 10^5$ | $9.3 \times 10^7$ | $3.1 \times 10^5$ | N/A | ND |
| retentate | 910 | 313 | 285 | 95% | $1.4 \times 10^5$ | $4.4 \times 10^7$ | $1.6 \times 10^5$ | 53% | ND |

TABLE 7

CHT Type II Mixed-Mode Chromatography (Brx 8)

| Fractions | Titer (mg/L) | Volume (mL) | Total enzyme units | % hPAP recovery | HCP Avg. ng/mL | HCP Total ng | HCP Avg. ng/mg | % HCP reduction | rDNA pg/mg |
|---|---|---|---|---|---|---|---|---|---|
| Load | 1358 | 320 | 435 | 100% | $5.0 \times 10^4$ | $1.6 \times 10^7$ | $3.7 \times 10^4$ | N/A | N/A |
| Flow through | 911 | 470 | 428 | 99% | $3.4 \times 10^3$ | $1.6 \times 10^6$ | $3.7 \times 10^3$ | 90% | 6.6 |
| Elution 1 | 101 | 130 | 13 | 3% | $3.4 \times 10^4$ | $4.4 \times 10^6$ | $3.4 \times 10^5$ | 73% | ND |

TABLE 8

CHT Type II Mixed-Mode Chromatography (Brx 9)

| Fractions | Titer (mg/L) | Volume (mL) | Total enzyme units | % hPAP recovery | HCP Avg. ng/mL | HCP Total ng | HCP Avg. ng/mg | % HCP reduction | rDNA pg/mg |
|---|---|---|---|---|---|---|---|---|---|
| Load | 929 | 300 | 279 | 100% | $1.2 \times 10^5$ | $3.6 \times 10^7$ | $1.3 \times 10^5$ | N/A | N/A |
| Flow through | 695 | 470 | 264 | 95% | $1.1 \times 10^4$ | $4.0 \times 10^6$ | $1.5 \times 10^4$ | 89% | 5.8 |
| Elution 1 | 201 | 130 | 16 | 6% | $1.1 \times 10^5$ | $8.8 \times 10^6$ | $5.5 \times 10^5$ | 76% | ND |

Example 5

Phenyl High Substitute (HS) Hydrophobic Interaction Chromatography (HIC) was used to remove HCP from hPAP. Approximately 400 mL (Brx 8) and approximately 370 mL (Brx 9) of the flow through plus wash fractions from CHT Type II column (total ~389 mg hPAP for Brx 8, and ~166 mg of hPAP for Brx 9) was diluted 2 fold with 2 M $K_2HPO_4$, pH 7.5 and then loaded onto a 80 mL (Brx 8) or a 53 mL (Brx 9) Phenyl HS column. The Phenyl HS column was previously sanitized with 1 N NaOH and equilibrated with 5 CV of a buffer of 1 M $K_2HPO_4$, pH 7.5. After loading the sample, the column was washed with 5 CV of a buffer of 0.56 M $K_2HPO_4$, pH 7.5. Then, proteins containing hPAP were eluted by using a buffer of 0.19 M $K_2HPO_4$, pH 7.5 for 3 CV. Four CV of a buffer of 25 mM Tris-HCl, pH 7.5 was used to strip off proteins bound tightly to the column. All fractions were collected and the flow rate was 15 mL/min (Brx 8) and 10 mL/min (Brx 9) or a linear flow rate of 175.4 cm/hour. Load, flow through, wash, and elution samples were analyzed for hPAP activity and HCP.

Approximately 87% (Brx 8) and 78% (Brx 9) of the loaded hPAP activity units were recovered in the elution peak fractions (Tables 9 and 10). No significant activity was recovered in the flow through fractions. About 5% (Brx 8) and 14% (Brx 9) of hPAP activity was detected from the wash and strip fractions combined. There was about 99% HCP reduction for both reactor samples in the elution peak fractions with the final HCP concentration of 45 (Brx 8) and 229 (Brx 9) ng of HCP/mg of hPAP. While not wishing to be bound by any particular theory, the data suggest Phenyl HS chromatography using step gradient elution is efficient for HCP removal from hPAP.

TABLE 9

Phenyl High Sub Hydrophobic Interaction Chromatography (Brx 8)

| Fractions | Titer (mg/L) | Volume (mL) | Total enzyme units | % hPAP recovery | HCP Avg. ng/mL | HCP Total ng | HCP Avg. ng/mg | % HCP reduction | rDNA pg/mg |
|---|---|---|---|---|---|---|---|---|---|
| Load | 972 | 400 | 389 | 100% | $1.5 \times 10^3$ | $6.0 \times 10^5$ | $2.0 \times 10^3$ | N/A | N/A |
| Elution | 1355 | 250 | 339 | 87% | 32 | $8.0 \times 10^3$ | 45* | 99% | N/A |

*Calcuation of this value is: 32/0.7001 = 45.
The 0.7001 is the hPAP titer before adjustment due to volume increase on dialysis which is consistent with the sample used for HCP analysis.

TABLE 10

Phenyl High Sub Hydrophobic Interaction Chromatography (Brx 9)

| Fractions | Titer (mg/L) | Volume (mL) | Total enzyme units | % hPAP recovery | HCP Avg. ng/mL | HCP Total ng | HCP Avg. ng/mg | % HCP reduction | rDNA pg/mg |
|---|---|---|---|---|---|---|---|---|---|
| Load | 449 | 370 | 166 | 100% | $7.5 \times 10^3$ | $2.8 \times 10^6$ | $1.9 \times 10^4$ | N/A | N/A |
| Elution | 997 | 130 | 130 | 78% | 128 | $1.7 \times 10^4$ | 229* | 99% | N/A |

*Calculation of this value is: 128/0.5583 = 229.
The 0.5583 is the hPAP titer before adjustment due to volume increase on dialysis which is consistent with the sample used for HCP analysis.

Example 6

Viral nanofiltration of hPAP was evaluated. Approximately 225 mL (Brx 8) and approximately 85 mL (Brx 9) of the elution fractions from phenyl HS column (total ~252 mg hPAP for Brx 8, and ~90 mg of hPAP for Brx 9) was loaded onto a OptiScale 40 Capsule as a pre-filtration step under a pressure of 5 Psi generated by a nitrogen stream. The flow rate was 2-3 mL/min. The filtered sample was then loaded onto a VireSolve Pro filter as the viral nano-filtration step under a pressure of 30 Psi generated by a nitrogen stream. The flow rate was 2-3 mL/min. Samples of load, after pre-filtration and after viral filtration were submitted for hPAP activity analysis.

Approximately 97% (Brx 8) and 96% (Brx 9) of the loaded hPAP activity units were recovered after the final viral filtration (Tables 11 and 12). While not wishing to be bound by any particular theory, the results show that the viral filtration step has no detrimental effect on the protein recovery of hPAP and that this step can be adapted into a hPAP purification process for viral clearance.

TABLE 11

Viresolve Pro Filtration (Brx 8)

| Fractions | Titer* (mg/L) | Volume (mL) | Total enzyme units | % hPAP recovery |
|---|---|---|---|---|
| Load | 1120 | 225 | 252 | 100% |
| Pre-filter | 1090 | 224 | 245 | 97% |
| Viral-filter | 1110 | 224 | 246 | 98% |

*Determined by A280.

TABLE 12

Viresolve Pro Filtration (Brx 9)

| Fractions | Titer* (mg/L) | Volume (mL) | Total enzyme units | % hPAP recovery |
|---|---|---|---|---|
| Load | 1070 | 85 | 91 | 100% |
| Pre-filter | 1040 | 84 | 88 | 96% |
| Viral-filter | 1040 | 84 | 87 | 96% |

*Determined by A280.

Example 7

A UF/DF step was performed to buffer exchange hPAP samples after viral filtration, such as described in Example 6. The step was performed to place hPAP in the formulation buffer.

Approximately 190 mL (Brx 8) and approximately 75 mL (Brx 9) hPAP samples after viral filtration was concentrated by approximately 3 fold. The concentrated sample was then buffer exchanged to 0.9% saline using a regenerated cellulose 30 kDa membrane. A sample of the load, permeates, and retentate were saved and submitted for hPAP activity and HCP analysis.

Approximately 91% (Brx 8) and 81% (Brx 9) of the loaded hPAP activity units were recovered in the retentate fractions (Tables 13 and 14). No significant activity was recovered in the permeate fractions. There was about 64% (Brx 8) and 63% (Brx 9) HCP reduction in retentate fractions with the final HCP concentration of 12 (Brx 8) and 36 (Brx 9) ng/mg hPAP. These results show that the final UF/DF step is efficient in buffer exchange to formulation buffer as well as removing of HCP.

TABLE 13

UF/DF (Brx 8)

| Fractions | Titer* (mg/L) | Volume (mL) | Total enzyme units | % hPAP recovery | HCP Avg. ng/mL | HCP Total ng | HCP Avg. ng/mg | % HCP reduction | rDNA pg/mg |
|---|---|---|---|---|---|---|---|---|---|
| Load | 1097 | 190 | 208 | 100% | 33 | $6.3 \times 10^3$ | 30 | N/A | ND |
| retentate | 3356 | 57 | 190 | 91% | 40 | $2.3 \times 10^3$ | 12 | 64% | ND |

*determined by A280.

TABLE 14

UF/DF (Brx 9)

| Fractions | Titer* (mg/L) | Volume (mL) | Total enzyme units | % hPAP recovery | HCP Avg. ng/mL | HCP Total ng | HCP Avg. ng/mg | % HCP reduction | rDNA pg/mg |
|---|---|---|---|---|---|---|---|---|---|
| Load | 1040 | 75 | 78 | 100% | 84 | $6.3 \times 10^3$ | 80 | N/A | ND |
| retentate | 2330 | 27 | 63 | 81% | 86 | $2.3 \times 10^3$ | 36 | 63% | ND |

*determined by A280.

Example 8

A scalable, CGMP compliant, fed-batch stirred tank bioreactor process was developed for the production of recombinant human PAP (hPAP) using the cell line AER285G5. The hPAP concentration at harvest was about 200-250 mg/L. All media used in the process were chemically defined, animal component free, and available as standard commercial products from a major supplier to the biopharmaceutical industry. In the process, the cell line is robust and its metabolic properties are well-suited to bioreactor operation. Oxygen supply and pH control requirements are well within the capacity of standard production bioreactors. Nutrient consumption rates and waste product accumulation are reasonable. The process was developed in 5 L stirred tank bioreactors configured and operated as scale-down models of production bioreactors and is expected to scale to production bioreactors without difficulty.

The bioreactor process began by expanding the seed train from a single vial of the Master Cell Bank in Growth Medium (Gibco CD FortiCHO/8 mM Glutamine) using shake flask suspension culture. Cultures were maintained between approximately $0.3\text{-}3.5\times10^6$ cells/mL with 2-3 passages per week. The seed train was expanded as a standard culture and used directly as the bioreactor inoculum to provide a seeding density of $0.4\text{-}1.0\times10^6$ cells/mL.

The initial volume in the bioreactor was 66% of the target final culture volume, of which 25% was the inoculum and 75% was Production Medium (Gibco CD FortiCHO/8 mM Glutamine/1% HT Supplement). Feed Medium (Gibco CD FortiCHO/20% GE ActiFeed A/2% GE ActiFeed B) was added as a bolus at the rate of 10% of the initial culture volume per feed addition. Feed medium additions were made on alternate days from day 3 through 11. The bioreactor was harvested on day 14, or when the viability fell below 70%, whichever occurred first.

Culture conditions were maintained at 37° C., pH 7.0±0.2, and dissolved oxygen >50% air saturation through the entire bioreactor run. Oxygen and carbon dioxide were delivered through a large-pore sparger to control dissolved oxygen and pH. Sodium bicarbonate (0.5M) was delivered to the surface of as required to control pH. Air was continuously delivered through the sparger at a fixed flow rate of 0.4% vvm. No overlay gassing was used in the development bioreactors but may be recommended for production bioreactors.

The cultures in the bioreactors were harvested and used for downstream and analytical development, and for production of research supplies of purified hPAP.

Equipment

Standard cell culture laboratory equipment was used for the process development. Shake flask suspension culture in vented, flat bottom Erlenmeyer flasks on orbital platform shakers in $CO_2$ incubators was the primary culture mode for culture maintenance, exploratory screening experiments, and seed train expansion.

Bioreactor process development was done in Sartorius A-Plus bioreactors with Sartorius Uni-Vessel 5 L working volume glass vessels. Bioreactor control was provided by individual Sartorius A-Plus bioreactor controllers. Bioreactor data were collected and managed by a networked Sartorius MFCS SCADA program. Vessels were fitted with standard electrochemical sensors for oxygen and pH, two pitched-blade impellers, L-sparge bars with 1.6 mm pores, harvest, and sampling tubes. Head plate ports above the liquid surface were used for additions of base, feeds, and cells. Dissolved oxygen control was by delivery of oxygen to the sparger. Control of pH was by delivery of carbon dioxide to the sparger and pump delivery of base solution through a head plate port. The effective rate of air, oxygen, and carbon dioxide delivery was controlled by the duty cycle of individual solenoid valves to provide a pulsed flow of these gases. The 5 L bioreactor configuration parameters are provided in Table 15.

TABLE 15

5 L Bioreactor Standard Configuration

| Parameter | Description |
| --- | --- |
| Vessel Working Volume | 5 L |
| Impellor Design | 45° Pitched Blade; 70 mm dia; 3 sector shape blades |
| Number of Impellors | 2 (at 1 L & 3 L working volume level) |
| Sparger Design | Large pore sparge bar (2 × 1.65 mm holes) |
| Overlay Gas | None |
| Sparge Carrier Gas | Air |
| Air Flow Rate | Max: 100 mL/min; Effective: Fixed - 20 mL/min |
| $O_2$ Flow Rate | Max: 500 mL/min; Effective: Variable - DO Control |
| $CO_2$ Flow Rate | Max: 20 mL/min; Effective: Variable - pH Control |
| Dissolved $O_2$ Control | $O_2$ flow to sparge |
| pH Control | $CO_2$ to sparge; 0.5 M $NaHCO_3$ to head plate |

Materials

All materials and supplies, other than the cells, were commercial products suitable for both research and for GMP production. Pre-sterilized disposable supplies (shake flasks, pipettes, filter assemblies, bags, etc.) were used for both maintenance and experimental cultures. Sterile solutions of Gibco CD FortiCHO, Gibco L-Glutamine, and Gibco HT Supplement solutions were obtained from Invitrogen. ActiFeed A and ActiFeed B were obtained from GE/PAA. Feed medium was prepared as 20% ActiFeed A/2% ActiFeed B diluted into FortiCHO. A research cell bank (RCB) of hPAP AER285G5 was developed for process development and for preparation of a CGMP Master Cell Bank. A development cell bank (DCB) was also prepared and used for experiments AER21 through AER27. Cells from the Master Cell Bank (MCB) were used for experiment AER28 and AER29.

Methods

All process development up to experiment AER27 was done with cells from the DCB. Cells from the MCB were used for AER28 and AER29. Standard laboratory cell culture procedures were used to maintain cells as shake flask suspension cultures for all maintenance cultures and screening experiments. The standard growth medium for culture maintenance, seed train expansion, and the base medium for bioreactors was Gibco CD FortiCHO/8 mM Gibco L-Glutamine/1% Gibco HT Supplement.

All bioreactor process development was done in 5 L stirred tank bioreactors. The basic configuration and operating conditions used have previously scaled up successfully to 100 L and 500 L production bioreactors.

Cell Line Development

A candidate production cell line, clone AER285G5, and two back-up candidates, clones AER284B7 and AER292B5, were developed. The cell lines were developed using a Chinese Hamster Ovary (CHO) mammalian cell expression system purchased from Invitrogen/Life Technologies. The DNA sequence for r-shPAP Variant 2 (SEQ ID NO:1) and a GIBCO® Freedom™ DG44 cell line development kit were selected for CHO cell expression. The Freedom™ DG44 cell line is from a GMP Master Cell Bank established by Life Technologies. The GIBCO® pOptiVEC™-TOPO® TA expression vector containing the DHFR gene was used to develop the r-shPAP expression vector.

Cells were transfected using the lipid-based system Freestyle MAX reagent to express hPAP. Stable cells were further derived using the dihydrofolate reductase (DHFR) technology to amplify expression. Cells were amplified using methotrexate (MTX), a folic acid antagonist, which is actively transported into the cell via the folate transporter.

The candidate production cell line, clone AER285G5, and two back-up candidates, clones AER284B7 and AER292B5, were characterized for productivity, culture properties, and stability. All cell line development work was done using chemically defined media and reagents free of animal-derived components. Research cell banks (RCB) were prepared for each clone. The AER285G5 RCB has been certified sterile (21 CFR 610.12 & USP <71> Sterility Tests) and free of mycoplasma (cultivable and non-cultivable by FDA Points to Consider). The tested cell bank is considered the development cell bank (DCB) and is qualified for preparation of a GMP Master Cell Bank (MCB) and for development of r-shPAP production processes.

r-shPAP Analytical Methods

The activity of r-shPAP was measured using the ENZCHEK® Phosphatase Assay kit (Life Technologies, Cat # E12020). The interim reference standard, R4, was produced from material produced in the upstream and downstream process demonstration campaigns. It was aliquoted and stored at −80° C.

Standard Methods

Cell Culture Procedures: Standard aseptic technique and cell culture practices were used to maintain cells as shake flask suspension cultures without antibiotics. Cell condition, density, and viability were determined by manual hemacytometer/Trypan blue exclusion and/or BioRad TC-10 Automated Cell Counter. The standard Nova 400 BioAnalyzer assay panel was used to monitor nutrient and catabolite concentrations. Unless stated otherwise, experiments were set up from cultures recovered from the DCB.

Standard practices to ensure project security include single use of disposable cell contact supplies, dedicated media for each project, and no concurrent open culture operations on multiple projects.

Culture Maintenance. To recover cells from frozen storage, the vial was quick thawed in a 37° C. water bath. The freeze medium was removed by dilution of the thawed cell suspension into 10 mL growth medium (GIBCO® CD Forti-CHO™/8 mM Gibco L-Glutamine), centrifugation (5 min/220×g, 1000 rpm-), and suspension of the cell pellet in growth medium to a cell density of 0.3–0.5×$10^6$ cells/mL in a 125 mL shake flask.

Maintenance cultures and shake flask experimental cultures were generally maintained as a 30 mL total culture volume in 125 mL shake flasks. Cultures were maintained at 37° C., 5% $CO_2$ in a non-humidified incubator at 125 rpm on an orbital platform shaker with a 0.75" stroke. Cells were passaged every 2-3 days to maintain a target cell density range generally between 0.3–3×$10^6$ cells/mL. At higher seed densities, the cells grow to densities of 3–4×$10^6$ cells/mL with no observable impact on culture properties in subsequent passes. Doubling times of 24-27 hrs were typical.

Development Cell Bank Preparation: The production cell line was frozen as RCB vials (AER285G5) and stored in liquid $N_2$ vapor phase.

Seed Train Preparation: During early development work, fresh maintenance cultures were prepared from the DCB approximately once a month. Early shake flask screening experiments and bioreactor process development used seed trains started from the maintenance cultures. Bioreactor process demonstration campaigns 1 and 2 used seed trains started from an MCB vial for each bioreactor campaign.

The seed train expansion for the demonstration bioreactor runs modeled the number of population doublings required to inoculate the production bioreactors (11-15 PDL). Seed trains were expanded in shake flask cultures up to 2 L shake flasks with culture volumes approximately 40% of the nominal flask volume.

Bioreactor Operation: The bioreactors were configured and operated as scale-down models of the 500 L production bioreactors. Configuration parameters common to all bioreactor runs are provided in Table 15. Default operating parameters common to all bioreactor runs are provided in Table 16. Experimental changes to the default parameters are described in the discussion of the appropriate experiment. All ports and dip tubes were fitted with weldable tubing to make sterile connections to the vessel during the run with a Terumo tubing welder. The assembled vessel is autoclaved without medium. All additions to the vessel (medium, cells, feeds, base, etc.) were made through sterile welded tubing connections. All open preparatory operations were done in a biosafety cabinet. After temperature equilibration and air saturation of the medium, the oxygen sensor was calibrated and the pH calibration was confirmed.

Bioreactors were monitored daily for cell density, viability, and metabolite profile. A daily 10 mL sample was taken before any additions were made to determine cell density, viability, metabolite profile, and to check pH and dissolved oxygen sensor calibration. An aseptic analytical sample was clarified by centrifugation (10 min/2000×g) and stored at −20° C. for assay of product concentration after completion of the bioreactor run. Two 1 mL and one 5 mL retain samples were taken each day and stored at −20° C. After addition of feed medium and glutamine, a second sample was taken for a post-feed metabolite profile.

TABLE 16

Default Bioreactor Operating Parameters

| Parameter | Description |
| --- | --- |
| pH | 7.00 ± 0.2 dead band for bioreactor |
| Dissolved Oxygen | ≥50% (air saturation) ± 0.3% dead band |
| Temperature | 37° C. ± 0.3% dead band |
| Agitation | 120 rpm |
| Initial Volume (Vi) | 3.0 L (Inoculum; Base Medium, Feed Medium) |
| Inoculum Volume | 750 mL (≤25% of Initial Volume) |
| Target Seed Density | 0.4-1.0 × $10^6$ cells/mL |
| Base Medium | CD-FortiCHO/8 mM Glutamine/1% HT |
| Glucose Supplement | Add Glucose to maintain 3-6 g/L Glucose |
| Daily Sample Volume | 15 mL (5 mL flush, 10 mL sample); 1-2 samples/day |

Experimental Methods

For all shake flask experiments cells were seeded in 125 ml flasks to an appropriate density in growth medium, and other supplements as desired. Medium without L-glutamine, HT, or feed supplementation is referred to as 'base medium' in the text. In batch mode experiments, no further supplementation with feed medium, glucose, or glutamine was done during the course of the experiment. Cultures in fed-batch experiments were supplemented as described below.

All cultures were incubated shaking at 125 rpm in a 37° C., 5% $CO_2$ incubator. In all experiments, samples of 1.2 ml were taken as indicated. Prior to taking each sample, sterile water was added to the culture to correct for an evaporative loss of about 1 mL/day. Each sample was assayed immediately for viable cell density, percent cell viability, and the Nova assay panel. An aseptic analytical sample was clarified by centrifugation and stored at −80° C. for assay of hPAP concentration after completion of the experiment.

Standard Shake Flask Base Medium Screen, Expt AER21: The base medium screen was a standard batch mode shake flask culture assay to determine the baseline hPAP productivity of cells in 13 base media (Table 17) from 6 different vendors. This assay was used as a reference to compare productivity to determine which base medium should be used for production in bioreactors.

All base media were supplemented with 8 mM L-Glutamine and 1×HT supplement. Glucose (45%) was added as required to maintain glucose concentration between 2-6 g/L, as measured by the Nova.

Shake flasks of each base medium were set up using cells from the development cell bank. Flasks were seeded at pass 13 (32 days) from thaw at $3\times10^5$ cells/mL in 30 mL total volume. Cultures were sampled on days 3, 5, 7, 10, 12, and harvested on Day 14.

TABLE 17

Base Medium Screen Matrix

| Flask | Base Media | Vendor/Pt | Days of Glucose Addition |
|---|---|---|---|
| 1 | ActiCHO P | PAA/U21-051 | 7 |
| 2 | BalanCD | Irvine/91128 | 10 |
| 3 | ExCell 302 | Sigma/14324C-500 ML | 3, 10 |
| 4 | ExCell ACF | Sigma/C5467 | 3 |
| 5 | FortiCHO | Invitrogen/A11483-01 | 7, 10 |
| 6 | HyCell | HyClone/SH30934.01 | N/A |
| 7 | OptiCHO | Invitrogen/12681-011 | 7 |
| 8 | PowerCHO2 | Lonza/12-771Q | 10 |
| 9 | ProCHO5 | Lonza/12-766Q | N/A |
| 10 | OptiCHO + 20% Feed A | Inv./12681-011/A10234-01 | 7 |
| 11 | OptiCHO + 20% Feed B | Inv./12681-011/A10240-01 | N/A |
| 12 | OptiCHO + 10% Feed A/ 10% Feed B | Inv./12681-011/A10234-01/ A10240-01 | N/A |
| 13 | FortiCHO + 15% Feed A/ 15% Feed B | Inv./A11483-01/A10234-01/ A10240-01 | N/A |

Feed Medium Screen, Expt AER23: The feed medium screen was a fed-batch mode shake flask productivity assay. The objective was to improve the performance of the base medium by enriching it with feed medium to better match the metabolic properties of the cell line. Cells were fully adapted to the base medium, but were not adapted to the supplemented media. Twelve combinations of base medium and feed medium were examined according to the matrix described in Table 18. Cells from the development cell bank were seeded into 30 mL cultures at pass 4 from thaw (10 days) at a seed density of $3\times10^5$ cells/mL All base media were supplemented with 8 mM L-Glutamine and 1×HT supplement. Glucose (45%) was added to maintain glucose concentration between 2-6 g/L as measured by the Nova.

Cultures were sampled on days 3, 5, 7, 9, 11, 12, 13, and harvested on day 14, or when viability was ≤50%. At termination of the culture, 10 mL of culture was aseptically clarified by centrifugation (10 min/2000×G) and stored at −20° C.

TABLE 18

Feed Medium Screen Matrix

| Flask | Base Media | Feed Supplement | Feed Days |
|---|---|---|---|
| 1 | ActiCHO P | 1% ActiFeed A/0.1% ActiFeed B | 3, 5, 7, 9, 11 |
| 2 | ActiCHO P | 2% ActiFeed A/0.2% ActiFeed B | 3, 5, 7, 9, 11 |
| 3 | ActiCHO P | 10% CD Efficient Feed C | 3, 5, 7, 9, 11 |
| 4 | BalanCD | 10% CHO Feed 1 | 3, 5, 7, 9, 11 |
| 5 | FortiCHO | 10% CD Efficient Feed C | 3, 5, 7, 9, 11 |
| 6 | FortiCHO | 1% ActiFeed A/0.1% ActiFeed B | 3, 5, 7, 9, 11 |
| 7 | HyCell | 10% CD Efficient Feed C | 3, 5, 7, 9, 11 |
| 8 | HyCell | 10% Cell Boost 2 | 3, 5, 7, 9, 11 |
| 9 | HyCell | 10% Cell Boost 4 | 3, 5, 7, 9, 11 |
| 10 | OptiCHO + 15% Feed B | 10% CD Efficient Feed B | 3, 5, 7, 9, 11 |
| 11 | OptiCHO + 15% Feed B | 10% CD Efficient Feed C | 3, 5, 7, 9, 11 |
| 12 | OptiCHO + 15% Feed C | 10% CD Efficient Feed C | 3, 5, 7, 9, 11 |

Feed Schedule Screen, Expt AER28: The feed schedule screen was a standardized fed-batch shake flask productivity assay. The objective was to identify feed medium and feed interval combinations that warrant further investigation in the controlled environment of bioreactors. The design of the feed schedule screen was independent of the results of the base medium screen and incorporates a separate evaluation of the effect of base medium supplementation when combined with short interval (2 day) and long interval (3 day) feed additions. A matrix of twelve combinations of multiple additions of Gibco Efficient FeedC or diluted ActiFeeds in a base medium of CD-FortiCHO/8 mM Glutamine/1% HT at intervals of two days or three days is used (Table 19). Diluted ActiFeed is a blend of 20% ActiFeed A and 2% ActiFeed B in CD Forti-CHO. Glucose was maintained >3 g/L not to exceed 6 g/L during the course of the experiment.

Cultures were seeded as pass 3 from thaw (8 days) with cells from the MCB at a seed density of $2.25\times10^5$ cells/mL in a 30 mL culture. Feeds were added to the cultures as defined in Table 19. No adjustments to the feed volume were made to compensate for the volume of culture removed by sampling.

Cultures were sampled on the days of feed addition and bi-daily after the last addition until viability was ≤50%. At termination of the culture, 10 mL of culture was aseptically clarified by centrifugation (10 min/2000×G) and stored at −20° C.

TABLE 19

Feed Schedule Matrix

| Flask | Base Media | Feed Medium** | Feed Schedule* |
|---|---|---|---|
| 1 | FortiCHO/8 mMGlut/HT | Diluted ActiFeeds (20%/2%) | 10% days 5, 7, 9, 11, 5% day 13 |
| 2 | FortiCHO/8 mMGlut/HT | Diluted ActiFeeds (20%/2%) | 5% days 5, 7, 9, 11, 13 |
| 3 | FortiCHO/8 mMGlut/HT | CD Efficient Feed C | 10% days 5, 7, 9, 11, 5% day 13 |
| 4 | FortiCHO/8 mMGlut/HT | CD Efficient Feed C | 5% days 5, 7, 9, 11, 13 |
| 5 | FortiCHO/8 mMGlut/HT | CD Efficient Feed C | 10% days 7, 9, 11, 13 |
| 6 | FortiCHO/8 mMGlut/HT | CD Efficient Feed C | 15% day 7 10% days 9, 11, 13 |

TABLE 19-continued

Feed Schedule Matrix

| Flask | Base Media | Feed Medium** | Feed Schedule* |
|---|---|---|---|
| 7 | FortiCHO/8 mMGlut/HT | Diluted ActiFeeds (20%/2%) | 10% days 7, 9, 11, 13 |
| 8 | FortiCHO/8 mMGlut/HT | Diluted ActiFeeds (20%/2%) | 15% day 7, 10% days 9, 11, 13 |
| 9 | FortiCHO/8 mMGlut/HT/ Insulin | Diluted ActiFeeds (20%/2%) | 10% days 5, 7, 9, 11, 5% day 13 |
| 10 | FortiCHO/8 mMGlut/HT/ Insulin | CD Efficient Feed C | 10% days 5, 7, 9, 11, 5% 13 |
| 11 | FortiCHO/8 mMGlut/HT | N/A | N/A |
| 12 | FortiCHO/8 mMGlut/HT/ Insulin | N/A | N/A |

*Feed medium additions in the Feed Schedule column are described as % (v/v) of the initial culture volume.
**The Diluted ActiFeeds medium composition in the Feed Medium column is described as the % (v/v) of the ActiFeed A and Actifeed B in FortiCHO.

Fed-Batch Bioreactor Operation: Five liter fed-batch bioreactors were used to evaluate and refine media and feed schedules selected from the shake flask screening experiments, and to produce material for purification development. The bioreactors were configured and operated as scale-down models of the 100 L and 500 L production bioreactors. Configuration parameters common to all bioreactor runs are provided in Table 15.

Default operating conditions are provided in Table 16. Except for pH and glucose addition, the default conditions were used for all bioreactor runs. Because there is no control operation when the process pH is in the dead band, the effective operating pH control point is the upper limit of the dead band early in the run and then drops to the lower limit of the dead band when acid generation becomes significant during the run. When acid generation and $CO_2$ removal are in reasonable balance, the pH may be any value within the dead band. Glucose was added as required to maintain the concentration in the 3-6 g/L range.

Bioreactors were sampled daily both before and after addition of feed medium. The first sample was assayed immediately for viable cell density, % cell viability, and the Nova assay panel. An aseptic analytical sample was clarified by centrifugation (10 min/2000×G) and stored at −20° C. for assay of product concentration after completion of the bioreactor run. The second sample was used only for the post-feed determination of the Nova panel of analytes.

Bioreactor runs were terminated on days 14-17, depending on the experiment. Viability of all reactors at harvest was over 50%. The cell-conditioned medium was aseptically harvested and transferred to Purification Development for clarification and use in purification development and production of research supplies of purified hPAP.

Results

General Culture Properties: Cells are robust and reach the maximum growth rate within 3 passages. The AER285G5 line maintains culture viability from thaw through seed train around 96%. Doubling times for this cell line are expected to be around 24 hours.

In CD FortiCHO/8 mM L-Glutamine, the cells from both the MCB and the DCB were generally easy to maintain in culture using standard culture practices with two (2) passages per week. The cultures were generally robust after thaw. The doubling time averaged approximately 24 hours. The seed train expansion should be 2-3 weeks from thaw to seeding of the bioreactor with passages every 3-4 days.

Base Medium Screen, Expt AER21: Supplementation of CD OptiCHO or CD FortiCHO feed media increased production, maximal cell density, and culture duration. However, non-supplemented HyCell CHO, ActiCHO and FortiCHO provided the best combination of productivity and culture performance for a production base medium. In batch shake flask cultures, the hPAP concentration at harvest was 71.3, 63, and 49.1 mg/L, respectively. Growth rates and peak cell densities were not comparable for these base media. The FortiCHO supported 45% more integrated cell-days than HyCell or ActiCHO.

As described above, AER21 was run as a batch shake flask culture with glucose supplementation during the experiment. The experiment was set up with cells from the development cell bank (DCB) at pass 13 from thaw. The assay results are summarized in Table 20. The data in Table 20 have been sorted by the day 14 hPAP concentration and have a different sequence of conditions than the Experimental Matrix (Table 18).

The three top conditions (1, 6, & 13) for hPAP concentration on day 14 are not well separated from the remaining conditions (Table 20). Of these, condition 1 & 6 are higher than conditions 13 for titer, however condition 13 outperformed 1 & 6 for culture properties. Condition 13 (FortiCHO/15% A/15% B) provided the highest peak viable cell densities of the top conditions (12.6×10$^6$/mL), relatively rapid growth rates (24.1 hr doubling time to day 3), and one of the higher specific productivities. Although the integrated cell days and culture duration of these top-producer conditions are good, condition 5 (FortiCHO) was the best for integrated cell days (150.6), peak density (17.1×10$^6$/ml), and culture duration. While not wishing to be bound to any particular theory, with the possible exception of condition 11 (OptiCHO/20% FeedB), there does not appear to be a clear performance advantage for either FeedA or FeedB when added at 20% concentration to OptiCHO, either as individual or combined additions.

The nutrient and metabolite levels are generally well-controlled for all conditions. Glucose was exhausted in most of the flasks at the time of harvest. Glutamine was also exhausted in most flasks, but low Glutamine did not negatively affect growth or productivity. Lactate, ammonia, and pH were exceptionally well-controlled in all conditions. The sodium concentration is constant for the entire assay period for all conditions and confirms the correct volume of water was added to adjust for evaporation. The change in osmolality is presumed to result from consumption of glucose and amino acids.

TABLE 20

Base Medium Screen Results

| Condition | Day 14 Titer (mg/L) | Spec Prod (pg/c/d) | ICD (e6 c-d/mL) | Peak VCD (e6/mL) | Day 3 Td (lar) | Culture Duration (days above 50% viable) |
|---|---|---|---|---|---|---|
| 6 | 71.3 | 0.9 | 81.8 | 9.79 | 22.9 | 12 |
| 1 | 64.0 | 0.8 | 81.5 | 11.6 | 23.6 | 12 |
| 13 | 62.7 | 0.6 | 100.2 | 12.6 | 24.1 | 12 |
| 11 | 59.6 | 0.5 | 112 | 13.6 | 17.3 | 12 |
| 2 | 55.9 | 0.5 | 106.2 | 12.2 | 23.1 | 14 |
| 3 | 53.5 | 0.8 | 70.9 | 8.65 | 20.8 | 14 |
| 5 | 49.1 | 0.3 | 150.6 | 17.1 | 20.6 | 14 |
| 12 | 47.8 | 0.5 | 101.8 | 12.2 | 20.8 | 12 |
| 8 | 40.5 | 0.8 | 48.4 | 5.75 | 22.1 | 12 |
| 9 | 29.5 | 0.5 | 61.9 | 8.1 | 21.4 | 14 |
| 10 | 27.6 | 0.3 | 88.9 | 10.8 | 23.2 | 14 |
| 7 | 24.9 | 0.3 | 78.5 | 11.7 | 19.8 | 7 |
| 4 | 24.2 | 0.9 | 26.2 | 3.68 | 26.4 | 14 |

Data are sorted by the Day 14 Titer rather than by experimental condition as in the experimental matrix and the figures.
The product concentration was determined using activity assay.
Data are from experiment AER21.

Feed Medium Screen, Expt AER23: 12 fed-batch shake flasks were set up to continue comparison of 5 base media for use as the production medium. Cultures were fed bi-daily beginning on day 3 with recommended feed media appropriate to each base medium platform. ActiCHO and HyCell CHO produced the highest titers reaching levels of 211.8 and 168.2 mg/L respectively. FortiCHO was mid-range in titer, however outperformed all other conditions for culture characteristics.

As described above, AER23 was run as a fed-batch shake flask culture with glucose supplementation during the experiment. The experiment was set up with cells from the development cell bank (DCB) at pass 4 from thaw. The assay results are summarized in Table 21. The data in Table 21 have been sorted by the day 14 hPAP concentration and have a different sequence of conditions than the Experimental Matrix.

The three top conditions (2, 3, &7) for hPAP concentration on day 14 are fairly well separated from the remaining conditions (Table 21). Of these, conditions 2 & 3 are higher than condition 7. Condition 2 also provided excellent peak viable cell densities 12.5×10⁶/mL (i.e., 12.5 e6/mL), relatively rapid growth rates (29.3 hr doubling time to day 3), and one of the highest specific productivities. Although the integrated cell days and culture duration of these top-producer conditions are good, condition 5 was also the best for integrated cell days or culture duration. While not wishing to be bound to any particular theory, with the possible exception of condition 10 (OptiCHO+15% FeedB), there does not appear to be a clear performance advantage for either FeedA or FeedB when added at 15% concentration, either as individual or combined additions.

The nutrient and metabolite levels were generally well-controlled for all conditions. Conditions 1 and 6, however, may have been limited by glucose exhaustion. Glutamine was also exhausted in most flasks, but low Glutamine did not negatively affect growth or productivity. Lactate, ammonia, and pH were exceptionally well-controlled in all conditions. The sodium concentration is constant for the entire assay period for all conditions and confirms the correct volume of water was added to adjust for evaporation. The change in osmolality is presumed to result from consumption of glucose and amino acids.

TABLE 21

Feed Medium Screen Results

| Condition | Day 14 Titer (mg/L) | Spec Prod (pg/c/d) | ICD (e6 c-d/mL) | Peak VCD (e6/mL) | Day 3 Td (hr) | Culture Duration (days) |
|---|---|---|---|---|---|---|
| 2 | 211.8 | 2.7 | 78.4 | 12.5 | 29.3 | 13 |
| 3 | 181.5 | 3.3 | 55 | 6.84 | 27.2 | 14 |
| 7 | 168.2 | 2.9 | 58.9 | 5.67 | 24.4 | 14 |
| 10 | 138.8 | 1.5 | 91.3 | 9.82 | 20.7 | 14 |
| 11 | 116.3 | 1.2 | 97.2 | 12 | 19.2 | 14 |
| 5 | 114.2 | 1.1 | 105.1 | 13.1 | 24.5 | 14 |
| 1 | 100.3 | 1.6 | 61.6 | 10.1 | 32.2 | 12 |
| 12 | 91.1 | 1.5 | 60 | 8.11 | 25 | 12 |
| 4 | 84.5 | 1.1 | 78.5 | 9.27 | 23.1 | 14 |
| 9 | 77.7 | 1.6 | 49.5 | 5.68 | 25.5 | 14 |
| 8 | 69.1 | 1.6 | 44.6 | 4.66 | 23.7 | 14 |
| 6 | 46.4 | 0.6 | 77.4 | 14.3 | 25 | 9 |

Data are sorted by the Day 14 Titer rather than by experimental condition as in the experimental matrix and the figures.
The product concentration was determined using activity assay.
Data are from experiment AER23.

Feed Schedule Screen, Expt AER28, Multi-Feed Screen: Among the feed media tested, the diluted ActiFeeds provided a significantly higher hPAP yield than CD Efficient Feed C with the same feed schedule. Both feed media showed good culture properties with high cell densities up to 18×10⁶ cells/ml and greater than 140 integrated cell days. Culture duration (16 days/80-90% viability) was good. The difference in product yield is approximately 20% between diluted ActiFeeds and Feed C.

The experiment was set up with cells from the Aerial MCB (Pass 3/Day 8 from thaw) using the feed schedule matrix defined in Table 19.

The results are summarized in Table 22. It should be noted that the design of this study varies the volume between feed additions, but the feed schedule is essentially the same for all conditions (maximal 50% of initial volume). Due to the feed schedule differences, the first day of feed addition ranges from day 5 to day 7 with all feeds completed by day 13.

Data from control cultures indicate that the general culture performance parameters of peak VCD and ICD in this study were comparable to the Feed Medium Screen study. Any difference in the initial growth rate is believed to reflect acceptable variations in the seed cultures and set up of the experiments. The highest hPAP titers are comparable or improved to those of the high production conditions in the Feed Medium Screen experiment (Table 21).

The most striking observation is the benefit of ActiFeed supplementation. All feed medium and feed schedule combinations which included ActiFeeds had a higher harvest hPAP concentration than any of the combinations that used CD Efficient Feed C. No other parameter had this perfect correlation with productivity. The directly measured culture parameters (peak VCD, culture duration, viability at harvest), and the derived culture parameters (doubling time, ICD, specific productivity), correlated positively to product yield in only a general sense. An increase in both ICD and specific productivity were required to maximize yield.

Among the highest yield conditions, the diluted ActiFeeds with a standard bi-daily addition beginning on day 5 provided significantly higher product yield and cellular specific productivity than other samples.

For the fed-batch conditions, hPAP yields do not appear to be limited by nutrient exhaustion or waste metabolite accumulation. Glucose concentrations at harvest were greater than 2 g/L and glutamate concentrations were greater than 2.5 mM. The peak lactate and ammonia concentrations were less than 2 g/L and 9 mM, respectively, values well below those frequently encountered in production bioreactors. The minimum pH ranged from 6.8 to 7.0, and the maximum pH was 7.2 to 7.4. Even though there was no attempt to actively control pH in this experiment, the pH remained within a range frequently used in production bioreactors and suggests pH control will not be difficult to achieve.

The significance of the apparent near exhaustion of glutamine is not clear. Gibco applications specialists acknowledged that components in the Efficient Feed Media interfere with determination of glutamine by the Nova bioanalyzer, but could not describe the nature of the interference. Based on Nova bioanalyzer measurements of glutamine before and after addition of glutamine to cultures, changes in concentration in the 2 mM to 8 mM range are can be measured and are relatively accurate. However, it appears the interference causes an elevated baseline at lower glutamine concentrations. The low residual concentrations of glutamine observed in this experiment may be artifacts of assay interference. Although glutamine consumption was initially rapid, it appeared to reach a steady state and no additional glutamine was added during the experiment. It is not clear, but the assays suggest that glutamine is not required as a nutrient supplement.

The results of the feed schedule screen, for the most part, appear to be internally consistent and in reasonable agreement with the results of the supplemented medium screen. Diluted ActiFeeds with 10% Vi bi-daily addition provides the most consistent improvement in hPAP production as the feed medium for fed-batch culture. In addition, the feed schedule screen demonstrated that supplementation of the base medium with insulin does not enhance the product yield.

While not wishing to be bound to any particular theory, based on both the feed screen and the base medium screen results, the most promising feed medium is diluted ActiFeeds. Further, without wishing to be bound to any particular theory, the most promising feed schedule is to supplement with 50% (Vi) feed medium and to add feed medium a the rate of 10% (v/v) per addition on a 2 day interval starting when cells are ½ maximal cell density which is typically around day 5.

TABLE 22

Fed-Batch Shake Flask Feed Schedule Screen Results

| ID | Base Medium | Feed | Feed Schedule (day) | Harvest Titer (mg/L) | ICD (e6 c-d /mL) | Spec Prod (pg/c/d) | Peak VCD (e6/mL) | Td Day 5 (hr) | Culture Dur. (days) | Harvest % Viable |
|---|---|---|---|---|---|---|---|---|---|---|
| 1 | FortiCHO | 10% Dil. AF | 5, 7, 9, 11, 13 | 181.9 | 158.6 | 1.1 | 18.2 | 30.5 | 16 | 84 |
| 9 | FortiCHO | 10% Dil. AF | 5, 7, 9, 11, 13 | 167.4 | 162.4 | 1.0 | 16.6 | 30.2 | 16 | 83 |
| 7 | FortiCHO | 10% Dil. AF | 7, 9, 11, 13 | 160.0 | 151.9 | 1.1 | 15.1 | 31.5 | 16 | 84 |
| 8 | FortiCHO | 15%/10% Dil. AF | 7, 9, 11, 13 | 152.3 | 164.4 | 0.9 | 17.8 | 35.6 | 16 | 85 |
| 2 | FortiCHO | 5% Dil. AF | 5, 7, 9, 11, 13 | 149.4 | 164.9 | 0.9 | 18.3 | 36 | 16 | 78 |
| 3 | FortiCHO | 10% Fd C | 5, 7, 9, 11, 13 | 147.5 | 138.4 | 1.1 | 15.1 | 36.3 | 16 | 82 |
| 10 | FortiCHO | 10% Fd C | 5, 7, 9, 11, 13 | 138.0 | 138.7 | 1.0 | 15.3 | 31.4 | 16 | 80 |
| 5 | FortiCHO | 10% Fd C | 7, 9, 11, 13 | 128.4 | 140.2 | 0.9 | 15.1 | 34.5 | 16 | 90 |
| 6 | FortiCHO | 15%/10% Fd C | 7, 9, 11, 13 | 123.6 | 126.1 | 1.0 | 12.2 | 33.7 | 16 | 87 |
| 4 | FortiCHO | 5% Fd C | 5, 7, 9, 11, 13 | 120.6 | 144.1 | 0.8 | 14.9 | 35.5 | 16 | 91 |
| 11 | FortiCHO | N/A | N/A | 120.3 | 129.9 | 0.9 | 14.7 | 31.1 | 13 | 49 |
| 12 | FoltiCHO | N/A | N/A | 113.5 | 158.3 | 0.7 | 16.6 | 32.3 | 16 | 67 |

Data are sorted by the Harvest Titer rather than by experimental condition as in the experimental matrix and the figures.
The hPAP concentration was determined using PAP activity assay. Data are from experiment AER28.

Example 9

A process for producing recombinant human PAP (hPAP) was performed on the bioreactor scale with nine separate bioreactors (Brx 1-9). Reference is made to equipment, materials, procedures, data, etc. in Example 8. Campaign 1 (bioreactors 1, 2, 3, and 4) and campaign 2 (bioreactor 5, 6, and 7) were process development campaigns which explored and refined fed-batch strategies suggested by the shake flask screening studies. Campaign 3 (bioreactors 8 and 9) was a process demonstration campaign to demonstrate process consistency and readiness for scale-up to production, and to produce supplies for demonstration of the purification process. All bioreactors were harvested and used for purification and assay development.

The feed schedules are provided in Table 23. All base media were supplemented with 8 mM L-glutamine and 1% HT Supplement.

TABLE 23

Bioreactor Feed Schedules

| Brx No. | Base Medium | Feed Medium | Feed Vol (% v/v) | Feed Schedule (day) | Glucose Feed (day) | Harv Day |
|---|---|---|---|---|---|---|
| 1 | ActiCHO P | Dil.ActiFeeds | 10 | 5, 7, 9, 11, 13 | 7, 10, 11, 15 | 16 |
| 2 | ActiCHO P | FeedC | 10 | 5, 7, 9, 11, 13 | 10 | 15 |

TABLE 23-continued

Bioreactor Feed Schedules

| Brx No. | Base Medium | Feed Medium | Feed Vol (% v/v) | Feed Schedule (day) | Glucose Feed (day) | Harv Day |
|---|---|---|---|---|---|---|
| 3 | HyCell CHO | FeedC | 10 | 5, 7, 9, 11, 13 | 10,12 | 14 |
| 4 | FortiCHO | FeedC | 10 | 5, 7, 9, 11, 13 | 10,15 | 17 |
| 5 | ActiCHO P | Dil ActiFeeds | 10 | 4, 6, 8, 10, 12 | 10,14 | 16 |
| 6 | ActiCHO P | FeedC | 10 | 4, 6, 8, 10, 12 | 12 | 15 |
| 7 | FortiCHO | Dil. ActiFeeds | 10 | 4, 6, 8, 10, 12 | 6, 10, 12, 14 | 15 |
| 8 | FortiCHO | Dil. ActiFeeds | 10 | 3, 5, 7, 9, 11, 13 | 6, 8, 10, 13, 15 | 16 |
| 9 | FortiCHO | Dil. ActiFeeds | 10 | 3, 5, 7, 9, 11, 13 | 6, 8, 11, 14 | 16 |

The bioreactor seed train details are provided in Table 24. The seed trains for bioreactor Campaigns 1 and 2 were thawed from the Development Cell Bank (DCB) and the seed train for Campaign 3 was thawed from the Master Cell Bank (MCB). Final Td is the doubling time (firs) of the last pass before inoculation of the bioreactor. Average Td is the doubling time is calculated by dividing the elapsed time from thaw to bioreactor inoculation by the PDL from thaw of the bank. Inoculum VCD and % V are for the inoculum culture immediately before inoculation of the bioreactor. Brx Seed VCD is the cell density measured in the bioreactor immediately after inoculation. The bioreactor performance is provided in Table 25.

TABLE 24

Bioreactor Seed Trains

| Brx No. | Cell Source | Passes from Thaw | Days from Thaw | Final Td (hrs) | Ave Td (hrs) | Inoc VCD (e6/ml) | Inoc % V | Brx Seed VCD (e6/mL) |
|---|---|---|---|---|---|---|---|---|
| 1 | DCB | 8 | 26 | | | 1.16 | 25 | 0.284 |
| 2 | DCB | 8 | 26 | | | 1.31 | 25 | 0.269 |
| 3 | DCB | 8 | 26 | | | 1.21 | 25 | 0.33 |
| 4 | DCB | 8 | 26 | | | 1.22 | 25 | 0.382 |
| 5 | DCB | 8 | 19 | | | 1.20 | 25 | 0.480 |
| 6 | DCB | 8 | 19 | | | 1.20 | 25 | 0.565 |
| 7 | DCB | 8 | 19 | | | 1.19 | 25 | 0.490 |
| 8 | MCB | 4 | 13 | | | 3.5 | 25 | 0.880 |
| 9 | MCB | 4 | 13 | | | 3.5 | 25 | 0.860 |

TABLE 25

Bioreactor Performance Summary

| Brx No. | ICD (e6 c-d/mL) | Peak VCD (e6/mL) | Peak VCD Day | Harvest Day | Harvest hPAP (mg/L) | Ave Sp. Prod. (pg/c/d) |
|---|---|---|---|---|---|---|
| 1 | 0.284 | 17.3 | 11 | 16 | 255.2 | 1.8 |
| 2 | 0.269 | 11.6 | 10 | 15 | 296.9 | 3.4 |
| 3 | 0.33 | 13.2 | 7 | 14 | 159.3 | 1.5 |
| 4 | 0.382 | 12.5 | 9 | 17 | 196.6 | 1.4 |
| 5 | 0.48 | 17.8 | 10 | 16 | 269.4 | 2.3 |
| 6 | 0.565 | 9.56 | 9 | 15 | 253.0 | 3.3 |
| 7 | 0.49 | 20.1 | 10 | 15 | 293.8 | 2.2 |
| 8 | 0.88 | 16.0 | 11 | 16 | 245.2 | 1.7 |
| 9 | 0.86 | 13.7 | 10 | 16 | 218.3 | 1.7 |

Seed Train Expansion and Fed-Batch Bioreactor Process

The hPAP seed train expansion and fed-batch bioreactor process for each campaign were carried out as described below. Where multiple criteria are provided, they are believed to be interchangeable and are provided to give flexibility in designing the manufacturing record.

Materials:

| Components | Manufacturer | Cat. No. |
|---|---|---|
| GIBCO ® CD FortiCHO ™ | Invitrogen | A1148301 |
| Gibco Glutamine | Invitrogen | 25030-081 |
| HT Supplement | Invitrogen | 11067-030 |
| ActiCHO Feed A, liquid | PAA/GE | U15-072 |
| ActiCHO Feed B, liquid | PAA/GE | U05-054 |
| Glucose, 45% | SAFC | G8769 |
| Sodium Bicarbonate, 7.5% | SAFC | 58761 |

Seed Train Growth Medium:

CD FortiCHO/8 mM Glutamine

| Component | Qty/1 L Medium |
|---|---|
| GIBCO ® CD FortiCHO ™ | 960.0 mL |
| Gibco Glutamine | 40.0 mL |

Production Medium:

CD FortiCHO/8 mM Glutamine/1% v/v HT Supplement

| Component | Vol/5 L Brx | Vol/50 L Brx | Vol/500 L Brx |
|---|---|---|---|
| GIBCO ® CD FortiCHO ™ | 2360 mL | 23.60 L | 236.0 L |
| Gibco Glutamine | 99 mL | 0.99 L | 9.9 L |
| Gibco HT Supplement 1% | 24 mL | 0.24 L | 2.4 L |

Production Feed Medium (Diluted ActiFeed):

CD FortiCHO/20% ActiFeed A v/v/2% ActiFeed B v/v

| Component | Vol/5 L Brx | Vol/50 L Brx | Vol/500 L Brx |
|---|---|---|---|
| GIBCO ® CD FortiCHO ™ | 1290 mL | 12.9 L | 129.0 L |
| GE/PAA ActiFeed A | 330 mL | 3.3 L | 33 L |
| GE/PAA ActiFeed B | 33 mL | 0.33 L | 3.3 L |

Seed Train Expansion:

Thaw rapidly, dilute quickly with Growth Medium, centrifuge, resuspend in 30 mL Seed train Medium and place in a flat based shake flask. Expand flask(s) every two to three days.

| | |
|---|---|
| Seed Density | 0.2-0.5 × 10⁶/mL |
| Split Density | 1.5-6.0 × 10⁶/mL |
| Growth Rate | ~28-30 hr average doubling time over expansion from thaw to bioreactor seed. |

| | |
|---|---|
| Expansion Duration | 18 days for 500 L bioreactor volume |
| Incubator | 37° C./5% $CO_2$ |
| Agitation | 150 rpm for 125 mL shake flask |
| | 130 rpm for 500 mL shake flasks |
| | 115 rpm for 1000 mL shake flasks |
| | 100 rpm for 2000 mL shake flasks. |

Fed-Batch Bioreactor Set Up:

| | |
|---|---|
| Sparger | Large Bubble: Sparge bar with drilled holes |
| WV | 93% of Maximum bioreactor working volume (465 L for 500 L bioreactor) |
| Vi | 71% of WV - Initial set up volume after addition of inoculum (330 L for 500 L bioreactor) |

| | 50 L Bioreactor | | 500 L Bioreactor |
|---|---|---|---|
| Production Base Medium | 75% Vi | (24.8 L) | (248.0 L) |
| Inoculum Volume | 25% | 8.2 L | 82 L |
| Inoculum Cell Density | 4.0-6.0 × $10^6$ cells/mL (5.0 × $10^6$ cells/mL preferred) | | |
| Inoculum % Viability | >95% | | |
| Inoculum Growth Rate | Td 23-27 hr is expected | | |
| Inoculum Population Doublings | predict 11 PDL to seed 50 L bioreactor at 1.0 × $10^6$ cells/mL | | |
| | predict 18 PDL to seed 500 L bioreactor at 1.0 × $10^6$ cells/mL | | |
| Seeding Density | 0.7 × $10^6$ cells/mL target (PD has seeded at 0.3-1.0 × $10^6$ cells/mL.) | | |

Feed Schedule:

| | |
|---|---|
| Feed Period | Feed began when cells reached a minimum viable cell density of at least 6.0 × $10^6$ vc/ml. Feeds continued every other day until a total of 6 × 10% Vi feeds have been administered. |

Feed Rate Schedule (if feeds begin on Day 3)

| | Culture Day | | | | | |
|---|---|---|---|---|---|---|
| | 3 | 5 | 7 | 9 | 11 | 13 |
| Feed Rate (Vi) | 10% | 10% | 10% | 10% | 10% | 10% |

Feed Rate Schedule (if feeds begin on Day 4)

| | Culture Day | | | | | |
|---|---|---|---|---|---|---|
| | 4 | 6 | 8 | 10 | 12 | 14 |
| Feed Rate (Vi) | 10% | 10% | 10% | 10% | 10% | 10% |

| | |
|---|---|
| Glucose Feed | As required to maintain 3-6 g/L; by daily Nova assay (estimate 1.7 L for 50 L/17 L for 500 L bioreactor; consumption Days 6, 8, 10, 13, and 15 in PD Demo Reactor) |
| Harvest | Day 16 or 70% viability, whichever is first |

| Bioreactor Operating Parameters: | |
|---|---|
| pH | 7.0 ± 0.2 |
| Acid | $CO_2$ |
| Base | 7.5% $NaHCO_3$ (Did not use any base in PD) |
| % DO | ≥50% |
| DO Control | by $O_2$ flow only |
| Temperature | 37° C. |
| Constant Air Sparge | 0.4% vvm of WV |

| Bioreactor Operating Parameters: | |
|---|---|
| Overlay Air | None |
| Agitation | 35 rpm in 500 L bioreactor |
| | (120 rpm in PD Bioreactors) |

Bioreactor Culture Properties:

The cells are generally robust and easy to maintain in culture. Growth rate is around 28-30 hour doubling times throughout the seed train. Cells were thawed into a 125 mL shake flask in 30 mL medium using the standard thaw procedure and allowed to incubate for 48 hours before the first passage. Following passage 1, the cells were expanded every two to three days until the bioreactor inoculation.

The model for this process description is PD Brx8. The maximal density observed in Brx6 was ~14.5–16×$10^6$/mL on days 7 through 11. Viability was very high, 80-99%, throughout culture. Diluted ActiFeed was delivered slowly (8 mL/min) to the PD bioreactors on days 3, 5, 7, 9, 11, and 13.

Glucose was added on days 6, 8, 10, 13, and 15. While not wishing to be bound to any particular theory, based on the PD bioreactor, it may be possible that a fixed addition of 3 L of 45% glucose on non-feed days will maintain glucose in the appropriate range in the 500 L bioreactor.

Base addition requirements for pH control were very low in the PD bioreactor due to low lactate concentrations. Only 20 mL 7.5% Sodium bicarbonate was added during the entire run. Lactate is not fully consumed at any point in the run and pH values maintain within the wide pH control band.

In the bioreactor, oxygen consumption was low for the first 5-6 days of the culture then peaked at around on day 6. In PD, oxygen demand for Brx8 reached ~500 mL/min on day 6. Oxygen demand remained around 300-500 mL/min for the remainder of the culture. While not wishing to be bound to any particular theory, oxygen transfer is not believed to be a problem in the manufacturing bioreactors.

Campaign 1—Bioreactors 1, 2, 3, & 4, Expt AER25

Campaign 1 evaluated fed-batch bioreactor performance using four strategies suggested by the shake flask screening experiments described in Example 8. Three base media (CD FortiCHO, ActiCHO P, and HyCell CHO) were compared using CD Efficient FeedC. ActiCHO P with diluted ActiFeeds showed promise in the shake flasks, so it was included in Bioreactor Campaign 1. The performance was comparable in some respects. Product yield, cell yield, and metabolic behavior were excellent, but differ significantly between the base media. ActiCHO and FortiCHO were selected for further development because there was evidence suggesting greater potential for productivity than HyCell CHO.

Bioreactors 1, 2, 3, and 4 evaluated three different base media as well as different feed strategies for ActiCHO. These conditions were selected because they provided the highest hPAP yield or best culture conditions in the Feed Schedule screen. HyCell CHO was included in campaign 1 because it showed such high specific productivity in the feed medium screen. FortiCHO had the best culture characteristics of any medium tested. ActiCHO P has shown the highest titers even though cell density and ICD values had been lower than FortiCHO.

The default operating conditions were used for both bioreactors. The seed train and fed-batch bioreactor operation were performed as described above. The default pH set point of 7.00±0.2 was used because the effective control range of 6.8-7.2 avoids the pH extremes seen the shake flask cultures (6.6 to 7.5) and is consistent with ranges commonly used for production.

Cell density, viability, and growth rate was similar in both bioreactors until day 3, after which growth in Bioreactor 1 and 2 slowed in comparison to bioreactors 3 and 4. Bioreactor 1 reached peak cell density at day 11, which was later than the others (Brx 2—day 10, Brx 3—day 7, Brx 4—day9). However, the peak cell density of Brx 1 was the highest of the group ($17.3 \times 10^6$ cells/mL vs. Brx 2, 3, and 4 which had peak densities of $11.6 \times 10^6$, $13.2 \times 10^6$, and $12.5 \times 10^6$ cells/mL respectively). The cell density hit plateaus in Bioreactors 2, 3, and 4 after the feeds began while in Bioreactor 1 the cells continued to grow slowly up to a day 10 peak. Bioreactors were harvested on days 14 (Brx3), 15 (Brx2), 16 (Brx1), and 17 (Brx4) based on viability (≤80%) to facilitate comparison, avoid protein degradation by proteases released from dying cells, and to provide material to begin purification development.

Differences between the Bioreactors in integrated cell days and product yield were as much as two-fold. Bioreactor 2 had approximately 20% higher hPAP concentration at harvest than Bioreactor 1, which was the second highest. All four bioreactors showed a constant increase in hPAP concentration throughout the run. While not wishing to be bound to any particular theory, there does seem to be an inhibitory effect on cell growth with the use of CD Efficient FeedC as is evidenced by Bioreactor 1 continuing to grow for an additional 5 days after feeds began compared to the other three bioreactors whose growth rates slowed significantly at this time.

A summary comparison of the bioreactor and shake flask results is provided in Table 26. The primary benefits of bioreactor operation over the shake flask experiments were to increase the productivity and culture duration.

While not wishing to be bound to any particular theory, the improved performance in the bioreactors is assumed to be primarily a consequence of avoiding inhibitory pH extremes and non-ideal dissolved oxygen concentrations. Although pH was maintained in a slightly narrower range in the bioreactors than the shake flasks cells, no environmental or metabolic parameter was clearly correlated with the improved cell densities.

TABLE 26

Fed-Batch Bioreactor and Shake Flask Comparison
Summary data from the Feed Medium screen and from Bioreactor Campaign 1 are compared.
Data are drawn from experiments AER23 and AER26.

| ID | Base Medium | Feed | Feed Schedule (day) | Harvest Titer (mg/L) | ICD (e6 c-d/mL) | Spec Prod (pg/c/d) | Peak VCD (e6/mL) | Doub. Time (hr)[2] | Culture Duration (days) | Harvest % Viable |
|---|---|---|---|---|---|---|---|---|---|---|
| Brx1 | ActiCHO P | Dil ActiFeeds | 5, 7, 9, 11, 13 | 255.2 | 142.3 | 1.8 | 17.3 | 25.5 | 16 | 65.5 |
| Brx2 | ActiCHO P | FeedC | 5, 7, 9, 11, 13 | 296.9 | 87.3 | 3.4 | 11.6 | 27.5 | 15 | 53.6 |
| Brx3 | HyCell CHO | FeedC | 5, 7, 9, 11, 13 | 159.3 | 103.1 | 1.5 | 13.2 | 20.8 | 14 | 58.6 |
| Brx4 | CD FortiCHO | FeedC | 5, 7, 9, 11, 13 | 196.6 | 136.6 | 1.4 | 12.5 | 22.5 | 17 | 70.9 |
| [1]2 | ActiCHO P | Dil ActiFeeds | 5, 7, 9, 11, 13 | 211.8 | 78.4 | 2.7 | 12.5 | 29.3 | 13 | 31.0 |
| [1]3 | ActiCHO P | FeedC | 5, 7, 9, 11, 13 | 181.5 | 55.0 | 3.3 | 6.84 | 27.2 | 14 | 70.0 |
| [1]7 | HyCell CHO | FeedC | 5, 7, 9, 11, 13 | 168.2 | 58.9 | 2.9 | 5.67 | 24.4 | 14 | 88.0 |
| [1]5 | CD FortiCHO | FeedC | 5, 7, 9, 11, 13 | 114.2 | 105.1 | 1.1 | 13.1 | 24.5 | 14 | 71.0 |

[1]Flask numbers from AER23.
[2]Doubling times at day 1 for bioreactors, day 3 for shake flasks.

Campaign 2—Bioreactors 5, 6, & 7, AER27

The objective for Bioreactor Development Campaign 2 was to continue exploration of base/feed combinations in the controlled environment of a bioreactor. ActiCHO provided a nice level of productivity in Campaign 1, but the growth characteristics provided by FortiCHO were enough not to omit it from consideration. In Campaign 2, ActiCHO continued to produce well with titers in the range of 250 mg/L for both feed strategies. However, FortiCHO with diluted ActiFeeds (Bioreactor 7) achieved a harvest titer of almost 300 mg/L.

Cells for Campaign 2 were taken from the DCB and bioreactors were seeded at passage 6, 19 days post-thaw. Bioreactors 5 and 6 of Campaign 2 mirrored Bioreactors 1 and 2 from Campaign 1 with a 1 day shift in the feed schedule. Bioreactor 7 used the same base medium as Bioreactor 4, but used the diluted ActiFeeds as feed instead of CD Efficient FeedC. All three reactors were seeded at a target seed density of $0.5 \times 10^6$ vc/ml. This slightly higher seed density allowed feeds to begin one day earlier than the previous bioreactor campaign. Each reactor was fed at 10Vi on days 4, 6, 8, 10, and 12.

Bioreactor 7 was superior to 5 and 6 throughout the run. Brx 7 was the highest for harvest titer (293.8 mg/L), peak density (20.1×10⁶/ml), ICD (135.4), and led in specific productivity until day12. ActiCHO+FeedC (Brx6) had higher specific productivity for the last 4 days of the run.

FeedC again showed growth inhibition as Brx6 only reached a peak density of 9.63×10⁶/ml compared to Brx5 which reached 17.8×10⁶/ml with the same base medium (ActiCHO P). The low VCD of Brx6 only allowed it to reach 75.9 integrated cell days compared to Brx5 (118.1 ICD) and Brx7 (135.4 ICD).

Metabolites and pH were well controlled in all bioreactors of Campaign 2. Glucose addition was only required once for Brx5 and Brx6 and three times for Brx7. None of the cultures generated a high level of ammonia. The osmolality was higher in Brx6 than the other two, which may explain its higher specific productivity toward the end of the run.

Campaign 3—Bioreactors 8 & 9, Expt AER29

Bioreactors 8 and 9 were run with identical parameters to replicate the planned fed-batch process of development Bioreactor 3. The seed train and bioreactor operating conditions were as described above. Glucose was maintained at 3-6 g/L by supplementation as required. Culture was seeded at 0.88×10⁶ vc/ml with a target of 1×10⁶ vc/ml with the objective of driving the titer higher by starting with more cells. The bioreactors were harvested at Day 16 with viability still high at approximately 85% for both reactors.

Bioreactor 8 peaked at 16×10⁶ cells/ml on day 11 and then declined slowly. Viability was stable and high throughout the run slowly declining after day 12 and was harvested at 85.6%. Bioreactor 9 peaked at 13.7×10⁶ cells/ml on day 10 and then declined slowly. Viability was stable and high throughout the run slowly declining after day 12 and was harvested at 85.1%. Bioreactor 9 had a dissolved oxygen (DO) probe failure on day 6 and was unable to control gas mixture for several hours. This failure was repaired and the culture continued growing but experienced a lag in cell density compared to Bioreactor 8 where the density was about 20% lower in 9 than in 8.

Product titer peaked at 245.2 mg/L on day 16 (harvest day) for bioreactor 8. Bioreactor 9 reached a titer of 218.3 mg/L at harvest.

Titers were 15-20% lower than Brx 7 of campaign 2. While not wishing to be bound to any particular theory, this difference may be variability between assays, but could be the feed medium diluent. In Brx 7, ActiFeeds were diluted in ActiCHO whereas in Brx's 8 & 9, feeds were diluted in FortiCHO. Overall, the cultures performed well with limited base addition, not much ammonia build-up, and normal osmolalities.

Glucose and glutamate concentrations were all well controlled. Glucose supplementation was required 4-5 times for each reactor when glucose levels fell below 3 g/L as measured by BGA analysis.

This Campaign demonstrated that the fed-batch process is stable and reproducible and that extending the culture past day 16 does not increase total yields significantly. While not wishing to be bound to any particular theory, it may be desirable to harvest before viability drops significantly.

Bioreactor Performance Consistency

Bioreactor hPAP yields in the demonstration bioreactors were consistently in the range of 200-250 mg/L at day 16, whereas the first development bioreactors were up to 300 mg/L. The cells in the demonstration reactors grew at nearly the same rate as observed in reactor 7 of campaign 2, which was the model for the process. The difference in harvest titer may be assay variability or due to the feed medium diluent.

The process should scale up to a 500 L reactor as it was developed using bioreactors configured and operated as scale-down models of production bioreactors.

The foregoing is illustrative of the present invention, and is not to be construed as limiting thereof. The invention is defined by the following claims, with equivalents of the claims to be included therein. All publications, patent applications, patents, patent publications, sequences identified by GenBank and/or SNP accession numbers, and other references cited herein are incorporated by reference in their entireties for all teachings relevant to the sentence and/or paragraph in which the reference is presented.

---

That which is claimed is:

1. A method for providing purified prostatic acid phosphatase (PAP) from a mixture comprising PAP, comprising subjecting the mixture comprising PAP to two or more chromatography steps selected from anion exchange chromatography, cation exchange chromatography, mixed-mode chromatography, and hydrophobic interaction chromatography, thereby providing purified PAP, wherein the purified PAP has a host cell protein content of less than about 100 ng/mg PAP and a host cell DNA content of less than about 100 pg/mg PAP.

2. The method of claim 1, wherein the subjecting step comprises
   contacting the mixture with an anion exchange chromatography medium;
   eluting at least a portion of the PAP from the anion exchange chromatography medium to obtain a first PAP sample;
   contacting at least a portion of the first PAP sample with a cation exchange chromatography medium;
   eluting at least a portion of the PAP from the cation exchange chromatography medium to obtain a second PAP sample;
   contacting at least a portion of the second PAP sample with a mixed-mode chromatography medium;
   eluting at least a portion of the PAP from the mixed-mode chromatography medium to obtain a third PAP sample;
   contacting at least a portion of the third PAP sample with a hydrophobic interaction chromatography medium; and
   eluting PAP from the hydrophobic interaction chromatography medium to obtain a fourth PAP sample.

3. The method of claim 2, wherein the anion exchange chromatography medium comprises a strong anion exchange functional group.

4. The method of claim 2, wherein the cation exchange chromatography medium comprises a strong cation exchange functional group.

5. The method of claim 2, wherein the mixed-mode chromatography medium comprises a ceramic hydroxyapatite mixed-mode resin.

6. The method of claim 2, wherein the hydrophobic interaction chromatography medium comprises an aryl functional group.

7. The method of claim 1, further comprising filtering the purified PAP using an ultrafiltration/diafiltration step.

8. The method of claim 1, wherein the two or more chromatography steps are column chromatography steps.

9. The method of claim 1, wherein the PAP is recombinant PAP.

10. The method of claim 1, wherein the mixture comprises cell culture medium.

11. The method of claim 1, wherein the purified PAP has a purity of greater than 60%.

12. The method of claim 1, wherein the method provides an overall recovery of PAP from the mixture of about 30% to about 50%.

13. The method of claim 1, wherein the purified PAP has a specific activity of at least about 200 to about 500 $\mu mol \cdot min^{-1}$ of 6,8-difluoro-4-methylumbelliferyl phosphate (DiFMUP)/mg PAP at a pH of 5.0.

14. The method of claim 1, wherein the PAP is secretory PAP that is optionally soluble.

15. A method for providing purified prostatic acid phosphatase (PAP) from a mixture comprising PAP, comprising subjecting the mixture comprising PAP to two or more different chromatography steps selected from anion exchange chromatography, cation exchange chromatography, mixed-mode chromatography, and hydrophobic interaction chromatography, thereby providing purified PAP,
   wherein the purified PAP has a host cell protein content of less than about 100 ng/mg PAP and a host cell DNA content of less than about 100 pg/mg PAP.

16. The method of claim 15, wherein the two or more different chromatography steps comprise cation exchange chromatography, anion exchange chromatography, mixed-mode chromatography, and hydrophobic interaction chromatography.

17. The method of claim 15, further comprising filtering the purified PAP using an ultrafiltration/diafiltration step.

18. The method of claim 15, wherein the purified PAP has a purity of greater than 60%.

19. The method of claim 15, wherein the method provides an overall recovery of PAP from the mixture of about 30% to about 50%.

20. The method of claim 15, wherein the purified PAP has a specific activity of at least about 200 to about 500 $\mu mol \cdot min^{-1}$ of 6,8-difluoro-4-methylumbelliferyl phosphate (DiFMUP)/mg PAP at a pH of 5.0.

21. A method for providing purified prostatic acid phosphatase (PAP) from a mixture comprising PAP, comprising:
  contacting the mixture comprising PAP with an anion exchange chromatography medium;
  eluting at least a portion of the PAP from the anion exchange chromatography medium to obtain a first PAP sample;
  contacting at least a portion of the first PAP sample with a cation exchange chromatography medium;
  eluting at least a portion of the PAP from the cation exchange chromatography medium to obtain a second PAP sample;
  contacting at least a portion of the second PAP sample with a mixed-mode chromatography medium;
  eluting at least a portion of the PAP from the mixed-mode chromatography medium to obtain a third PAP sample;
  contacting at least a portion of the third PAP sample with a hydrophobic interaction chromatography medium; and
  eluting PAP from the hydrophobic interaction chromatography medium to obtain a fourth PAP sample, thereby providing purified PAP.

22. The method of claim 21, wherein the anion exchange chromatography medium comprises a strong anion exchange functional group.

23. The method of claim 21, wherein the cation exchange chromatography medium comprises a strong cation exchange functional group.

24. The method of claim 21, wherein the mixed-mode chromatography medium comprises a ceramic hydroxyapatite mixed-mode resin.

25. The method of claim 21, wherein the hydrophobic interaction chromatography medium comprises an aryl functional group.

26. The method of claim 21, further comprising filtering the fourth PAP sample using an ultrafiltration/diafiltration step.

27. The method of claim 21, wherein the purified PAP has a purity of greater than 60%.

28. The method of claim 26, wherein the purified PAP has a host cell protein content of less than about 100 ng/mg PAP and a host cell DNA content of less than about 100 pg/mg PAP.

29. The method of claim 21, wherein the method provides an overall recovery of PAP from the mixture of about 30% to about 50%.

30. The method of claim 21, wherein the purified PAP has a specific activity of at least about 200 to about 500 $\mu mol \cdot min^{1}$ of 6,8-difluoro-4-methylumbelliferyl phosphate (DiFMUP)/mg PAP at a pH of 5.0.

* * * * *

UNITED STATES PATENT AND TRADEMARK OFFICE
CERTIFICATE OF CORRECTION

PATENT NO. : 8,859,252 B1
APPLICATION NO. : 14/146165
DATED : October 14, 2014
INVENTOR(S) : Mitschelen et al.

It is certified that error appears in the above-identified patent and that said Letters Patent is hereby corrected as shown below:

In the Specification:

Column 37, Line 51: Please correct "cells/mL" to read -- cells/mL. --

Column 38, Line 43: Please correct ">3 g/L" to read -- $\geq$3 g/L --

Signed and Sealed this
Third Day of March, 2015

Michelle K. Lee
*Deputy Director of the United States Patent and Trademark Office*

SEQUENCE LISTING

```
<160> NUMBER OF SEQ ID NOS: 2

<210> SEQ ID NO 1
<211> LENGTH: 1161
<212> TYPE: DNA
<213> ORGANISM: Homo sapiens

<400> SEQUENCE: 1
atgagagctg cacccctcct cctggccagg gcagcaagcc ttagccttgg cttcttgttt      60
ctgctttttt tctggctaga ccgaagtgta ctagccaagg agttgaagtt tgtgactttg     120
gtgtttcggc atggagaccg aagtcccatt gacacctttc ccactgaccc cataaaggaa     180
tcctcatggc cacaaggatt tggccaactc acccagctgg gcatggagca gcattatgaa     240
cttggagagt atataagaaa gagatataga aaattcttga atgagtccta taaacatgaa     300
caggtttata ttcgaagcac agacgttgac cggactttga tgagtgctat gacaaacctg     360
gcagccctgt tcccccaga aggtgtcagc atctggaatc ctatcctact ctggcagccc     420
atcccggtgc acacagttcc tctttctgaa gatcagttgc tatacctgcc tttcaggaac     480
tgccctcgtt ttcaagaact tgagagtgag actttgaaat cagaggaatt ccagaagagg     540 ctgcacccctt ataaggattt tatagctacc ttgggaaaac tttcaggatt acatggccag     600
gacctttttg gaatttggag taaagtctac gacccttat attgtgagag tgttcacaat     660
```

-continued

```
ttcactttac cctcctgggc cactgaggac accatgacta agttgagaga attgtcagaa      720
ttgtccctcc tgtccctcta tggaattcac aagcagaaag agaaatctag gctccaaggg      780
ggtgtcctgg tcaatgaaat cctcaatcac atgaagagag caactcagat accaagctac      840
aaaaaactca tcatgtattc tgcgcatgac actactgtga gtggcctaca gatggcgcta      900
gatgtttaca acggactcct tcctccctat gcttcttgcc acttgacgga attgtacttt      960 gagaagggggg agtactttgt ggagatgtac tatcggaatg agacgcagca cgagccgtat    1020
cccctcatgc tacctggctg cagccccagc tgtcctctgg agaggtttgc tgagctggtt    1080
ggccctgtga tccctcaaga ctggtccacg gagtgtatga ccacaaacag ccatcaaggt    1140
actgaagaca gtacagatta g                                              1161
```

<210> SEQ ID NO 2
<211> LENGTH: 386
<212> TYPE: PRT
<213> ORGANISM: Homo sapiens

<400> SEQUENCE: 2

```
Met Arg Ala Ala Pro Leu Leu Leu Ala Arg Ala Ala Ser Leu Ser Leu
1               5                   10                  15

Gly Phe Leu Phe Leu Leu Phe Phe Trp Leu Asp Arg Ser Val Leu Ala
            20                  25                  30

Lys Glu Leu Lys Phe Val Thr Leu Val Phe Arg His Gly Asp Arg Ser
        35                  40                  45

Pro Ile Asp Thr Phe Pro Thr Asp Pro Ile Lys Glu Ser Ser Trp Pro
    50                  55                  60

Gln Gly Phe Gly Gln Leu Thr Gln Leu Gly Met Glu Gln His Tyr Glu
65                  70                  75                  80

Leu Gly Glu Tyr Ile Arg Lys Arg Tyr Arg Lys Phe Leu Asn Glu Ser
                85                  90                  95

Tyr Lys His Glu Gln Val Tyr Ile Arg Ser Thr Asp Val Asp Arg Thr
            100                 105                 110

Leu Met Ser Ala Met Thr Asn Leu Ala Ala Leu Phe Pro Pro Glu Gly
        115                 120                 125

Val Ser Ile Trp Asn Pro Ile Leu Leu Trp Gln Pro Ile Pro Val His
    130                 135                 140

Thr Val Pro Leu Ser Glu Asp Gln Leu Leu Tyr Leu Pro Phe Arg Asn
145                 150                 155                 160

Cys Pro Arg Phe Gln Glu Leu Glu Ser Glu Thr Leu Lys Ser Glu Glu
                165                 170                 175

Phe Gln Lys Arg Leu His Pro Tyr Lys Asp Phe Ile Ala Thr Leu Gly
            180                 185                 190

Lys Leu Ser Gly Leu His Gly Gln Asp Leu Phe Gly Ile Trp Ser Lys
        195                 200                 205

Val Tyr Asp Pro Leu Tyr Cys Glu Ser Val His Asn Phe Thr Leu Pro
    210                 215                 220

Ser Trp Ala Thr Glu Asp Thr Met Thr Lys Leu Arg Glu Leu Ser Glu
225                 230                 235                 240

Leu Ser Leu Leu Ser Leu Tyr Gly Ile His Lys Gln Lys Glu Lys Ser
                245                 250                 255

Arg Leu Gln Gly Gly Val Leu Val Asn Glu Ile Leu Asn His Met Lys
            260                 265                 270

Arg Ala Thr Gln Ile Pro Ser Tyr Lys Lys Leu Ile Met Tyr Ser Ala
```

-continued

```
                275                 280                 285
His Asp Thr Thr Val Ser Gly Leu Gln Met Ala Leu Asp Val Tyr Asn
    290                 295                 300

Gly Leu Leu Pro Pro Tyr Ala Ser Cys His Leu Thr Glu Leu Tyr Phe
305                 310                 315                 320

Glu Lys Gly Glu Tyr Phe Val Glu Met Tyr Tyr Arg Asn Glu Thr Gln
                325                 330                 335

His Glu Pro Tyr Pro Leu Met Leu Pro Gly Cys Ser Pro Ser Cys Pro
                340                 345                 350

Leu Glu Arg Phe Ala Glu Leu Val Gly Pro Val Ile Pro Gln Asp Trp
            355                 360                 365

Ser Thr Glu Cys Met Thr Thr Asn Ser His Gln Gly Thr Glu Asp Ser
    370                 375                 380

Thr Asp
385
```